(12) United States Patent
Hagihara et al.

(10) Patent No.: US 9,868,933 B2
(45) Date of Patent: Jan. 16, 2018

(54) CELL CULTURING METHOD, CELL CULTURING APPARATUS AND KIT COMPRISING A POROUS POLYIMIDE FILM

(71) Applicant: UBE Industries, Ltd., Ube-shi, Yamaguchi (JP)

(72) Inventors: Masahiko Hagihara, Ube (JP); Tetsuo Kawaguchi, Ube (JP); Kousuke Baba, Ube (JP); Motohisa Shimizu, Ube (JP)

(73) Assignee: UBE INDUSTRIES, LTD. (JP)

( * ) Notice: Subject to any disclaimer, the term of this patent is extended or adjusted under 35 U.S.C. 154(b) by 0 days.

(21) Appl. No.: 14/907,432

(22) PCT Filed: Jul. 25, 2014

(86) PCT No.: PCT/JP2014/070407
§ 371 (c)(1),
(2) Date: Jan. 25, 2016

(87) PCT Pub. No.: WO2015/012415
PCT Pub. Date: Jan. 29, 2015

(65) Prior Publication Data
US 2016/0168560 A1    Jun. 16, 2016

(30) Foreign Application Priority Data
Jul. 26, 2013 (JP) .................. 2013-155550

(51) Int. Cl.
| | | |
|---|---|---|
| *C12N 5/00* | (2006.01) | |
| *C12M 1/12* | (2006.01) | |
| *C12N 1/16* | (2006.01) | |
| *C12N 1/20* | (2006.01) | |
| *C12N 11/08* | (2006.01) | |
| *C08L 79/08* | (2006.01) | |

(52) U.S. Cl.
CPC ........... *C12N 5/0068* (2013.01); *C12M 25/02* (2013.01); *C12N 1/16* (2013.01); *C12N 1/20* (2013.01); *C12N 11/08* (2013.01); *C08L 79/08* (2013.01); *C12N 2533/30* (2013.01)

(58) Field of Classification Search
CPC .......... C12M 25/02; C12N 1/16; C12N 11/08; C12N 1/20; C12N 2533/30
USPC ... 435/180, 252.1, 252.5, 252.8, 255.1, 348, 435/395, 420
See application file for complete search history.

(56) References Cited

U.S. PATENT DOCUMENTS

| | | | |
|---|---|---|---|
| 4,533,637 A * | 8/1985 | Yamane | C07K 14/555 435/371 |
| 5,807,406 A | 9/1998 | Brauker et al. | |
| 2011/0290112 A1* | 12/2011 | Liu | B01D 53/228 95/54 |
| 2011/0318556 A1* | 12/2011 | Ohya | C08J 9/28 428/216 |

FOREIGN PATENT DOCUMENTS

| | | | |
|---|---|---|---|
| JP | 63-196273 | A | 8/1988 |
| JP | 63-196286 | * | 8/1988 |
| JP | A-63-196286 | | 8/1988 |
| JP | A-63-198975 | | 8/1988 |
| JP | A-63-198978 | | 8/1988 |
| JP | A-10-507111 | | 7/1998 |
| JP | 2009-213421 | A | 9/2009 |
| JP | A-2009-213421 | | 9/2009 |
| JP | A-2011-219585 | | 11/2011 |
| JP | A-2011-219586 | | 11/2011 |
| WO | WO 2009/123349 | A1 | 10/2009 |
| WO | WO 2010/038873 | A1 | 4/2010 |

OTHER PUBLICATIONS

Yabu et al. Preparation of Honeycomb-Patterned Polyimide Films by Self-Organization. Langmuir (2003), v19, p. 6297-6300.*
Baby Hamster Kidney Fibroblast Cells (BHK-21 line) (2004), 2 pages.*
Blasey et al. Strategies to Increase the Efficiency of Membrane Aerated and Perfused Animal Cell Bioreactors by an Improved Medium Perfusion. Animal Cell Culture and Production of Biologicals (1991), p. 61-73.*
Alberts et al. From DNA to RNA Molecular Biology of the Cell 4th Edition, NCBI Bookshelf ID NBK26887, 29 page reprint.*
W. Stromer. Trypan Blue Exclusion Test of Cell Viability. Current Protocols in Immunology (1997), Supplement 21, A.3B.1-A.3B.2.*
Sterile. (2011). In The Editors of the American Heritage Dictionaries (Ed.), The American Heritage Dictionary of the English language. Boston, MA: Houghton Mifflin.*
Biological Buffers (2000, 2 pages).*
Eagle's MEM medium by ATCC (2011, 2 pages).*
Inloes et al. Hollow-Fiber Membrane Bioreactors Using Immobilized E. coli for Protein Synthesis. Biotechnology and Bioengineering (1983), v25, p. 2653-2681.*
Tao et al. Polyetherimide membrane formation by the cononsolvent system and its biocompatibility of MG63 cell line. Journal of Membrane Science (2006), v269, p. 66-74.*

(Continued)

*Primary Examiner* — Sean C Barron
(74) *Attorney, Agent, or Firm* — Merchant & Gould P.C.

(57) ABSTRACT

The present invention relates to a cell culturing method and cell culturing apparatus and kit for use therewith. The method includes applying cells on a porous polyimide film and culturing. One embodiment includes a process for sowing cells on the surface of the film. Another embodiment includes a process for placing a cell suspension on the dried surface of the film and leaving the film undisturbed, moving the film to promote liquid efflux, or stimulating a portion of the surface to entangle the cell suspension into the film, and then retaining the cells in suspension inside the film while allowing moisture to flow out. Another embodiment includes a process for moistening one or both surfaces of the film with a cell culture solution or sterilized liquid, loading a cell suspension on the moistened film, retaining the cells in suspension inside the film, and allowing moisture to flow out.

19 Claims, 20 Drawing Sheets

(56) References Cited

OTHER PUBLICATIONS

Tao et al., "Polyetherimide membrane formation by the cononsolvent system and its biocompatibility of MG63 cell line," *Journal of Membrane Science* 269: 66-74 (2006).

Julien et al., "Implantation of ultrathin, biofunctionalized polyimide membranes into the subretinal space of rats," *Biomaterials*, 32:3890-3898 (2011).

Kawakami et al., "Cell Culture on Nano- or Micro-relief pattern Surface," *Membrane*, 32(5):266-270 (2007).

Seifert et al., "Polyetherimide: A New Membrane-Forming Polymer for Biomedical Applications," *Artificial Organs*, 26(2):189-199 (2002).

International Search Report for PCT/JP2014/070407 (mailed Oct. 21, 2014).

Subrizi et al., "Generation of hESC-derived retinal pigment epithelium on biopolymer coated polyimide membranes," Biomaterials, 33:8047-8053 (2012).

Krasteva et al., "Membranes for biohybrid liver support systems—investigations on hepatocyte attachment, morphology and growth," Biomaterials, 23:2467-2478 (2002).

European Search Report for EP 14 83 0076 (mailed Mar. 2, 2017).

Office Action for Korean Patent Application No. 10-2016-7001673 (dated Apr. 27, 2017).

\* cited by examiner

Fig. 1

Mode of seeding cell suspension on porous polyimide film – 1: Natural seeding

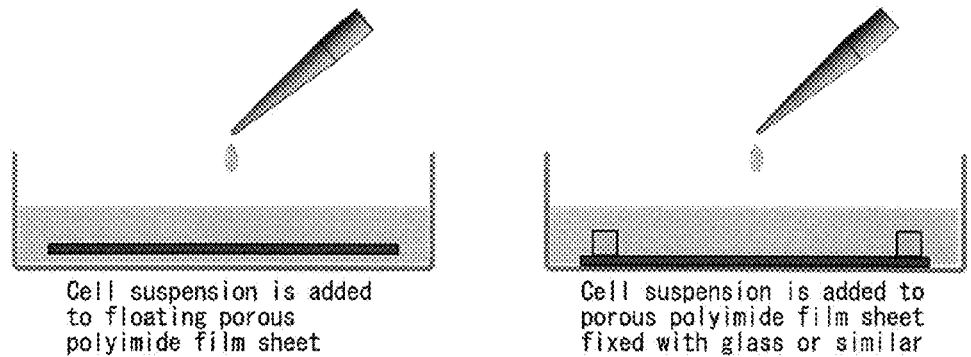

Cell suspension is added to floating porous polyimide film sheet

Cell suspension is added to porous polyimide film sheet fixed with glass or similar

Fig. 2

Mode of seeding cell suspension on porous polyimide film – 2: Suction seeding

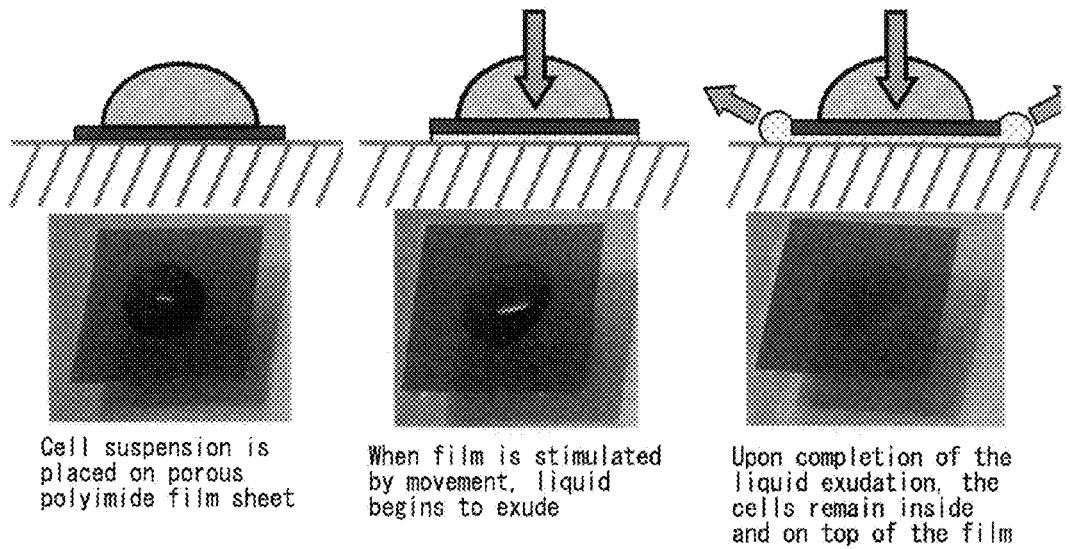

Cell suspension is placed on porous polyimide film sheet

When film is stimulated by movement, liquid begins to exude

Upon completion of the liquid exudation, the cells remain inside and on top of the film

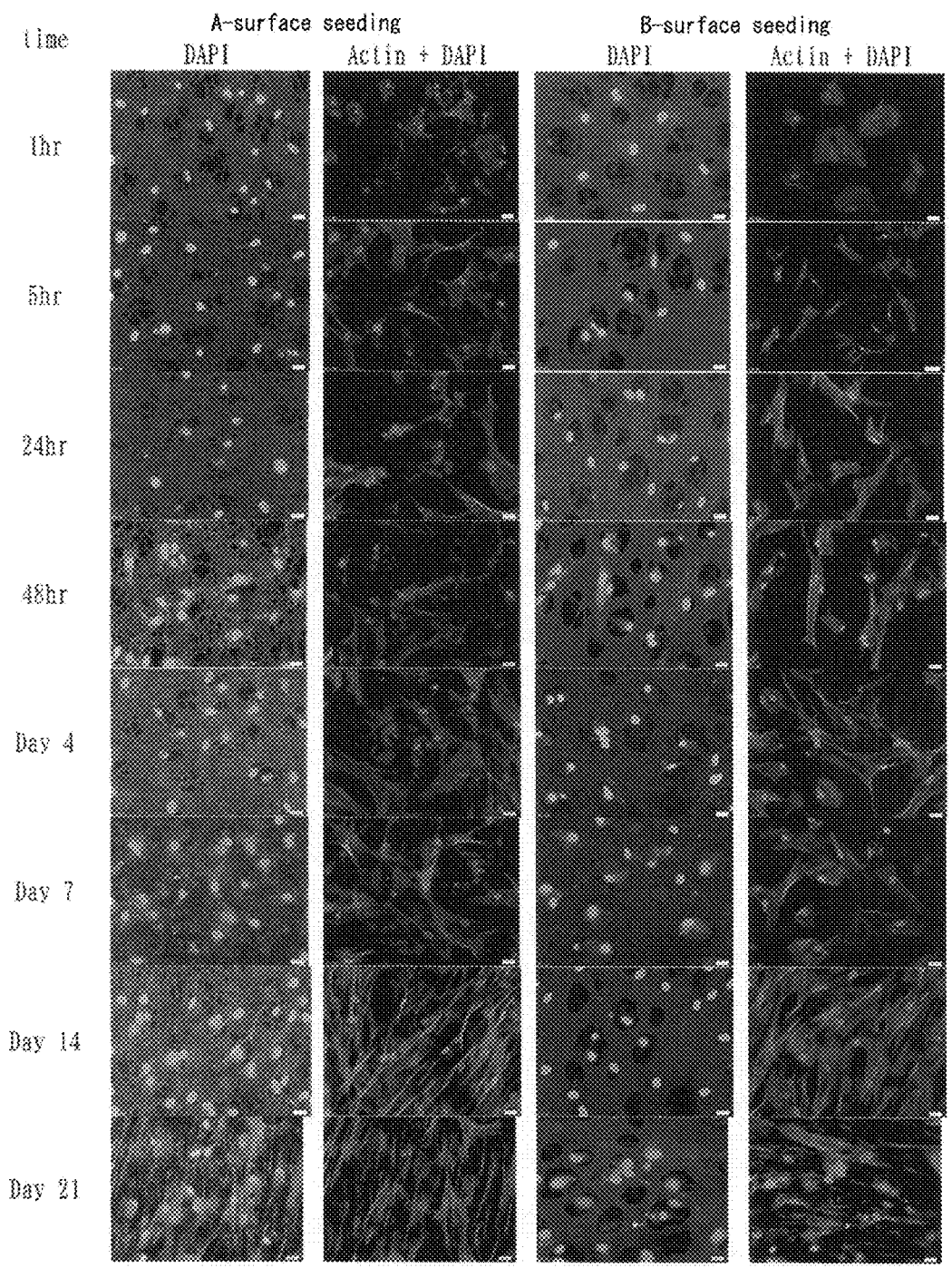
Fig. 3 Time-dependent changes in natural seeding of human mesenchymal stem cells, according to type of seeding surface

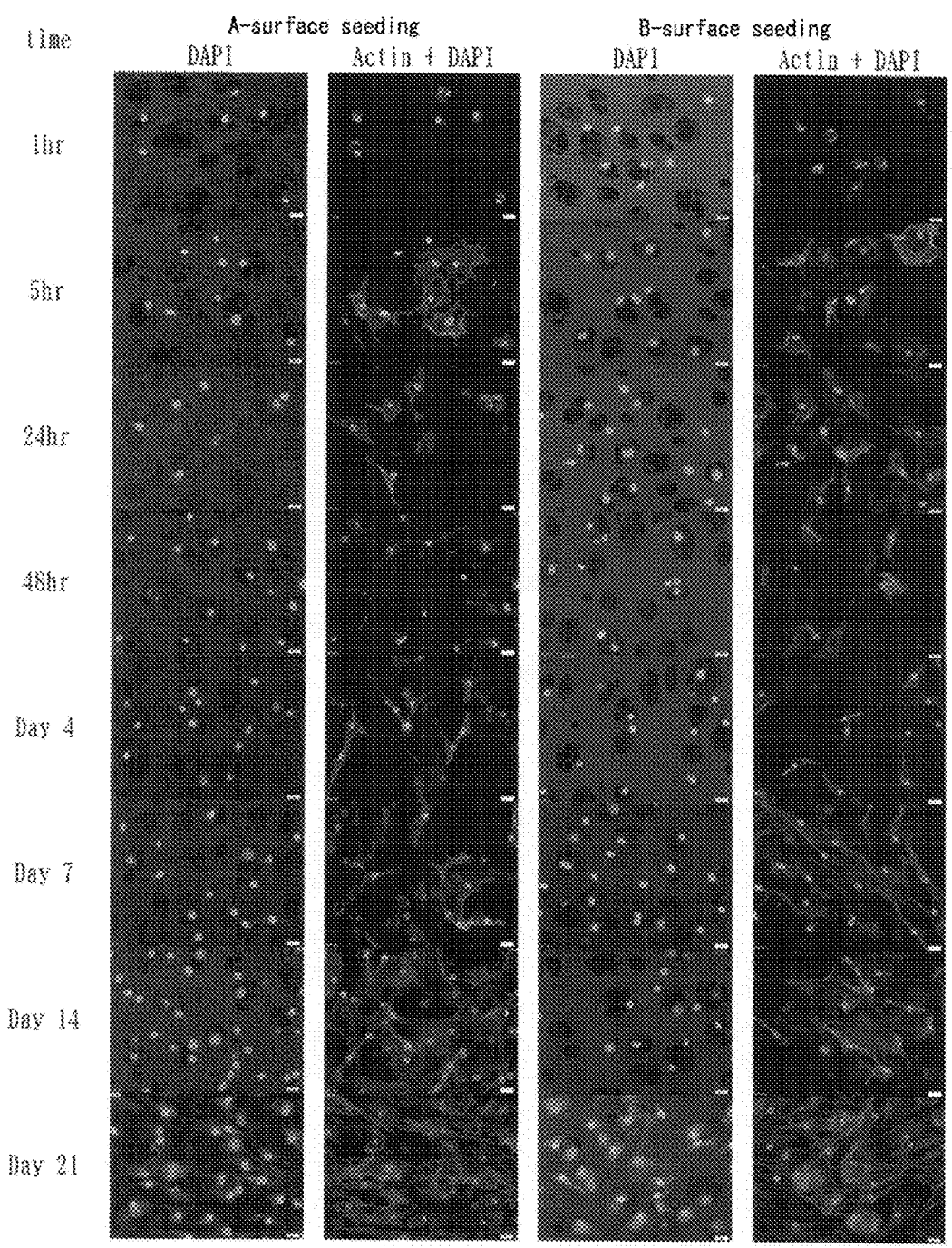

Fig. 5  Observation results with B-surface seeding of human skin fibroblasts (after 24 hours): Wet film method Observation conditions — Actin + DAPI Stereo fluorescent microscope

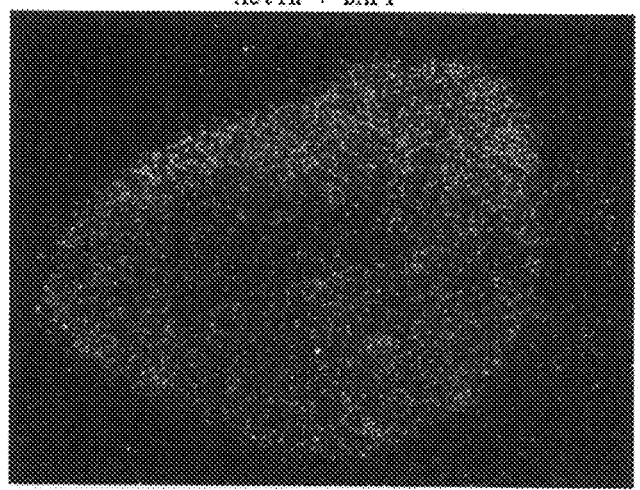

Observation conditions — DAPI — Actin + DAPI

Fluorescent microscope, center section, deep focus X20

Fluorescent microscope, center section, shallow focus X20

Fluorescent microscope, border section X10

Fluorescent microscope, border section X10

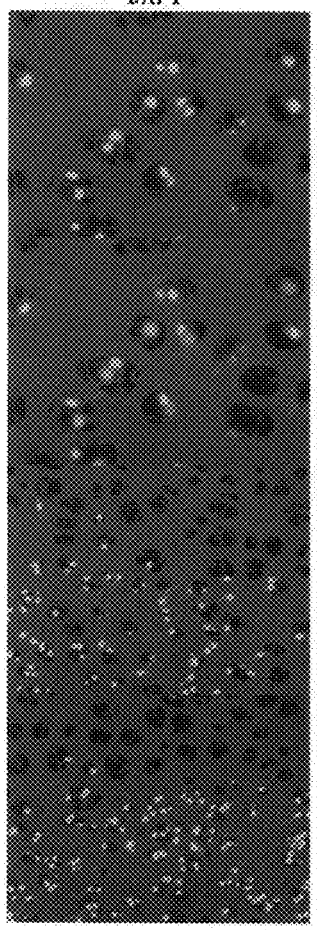
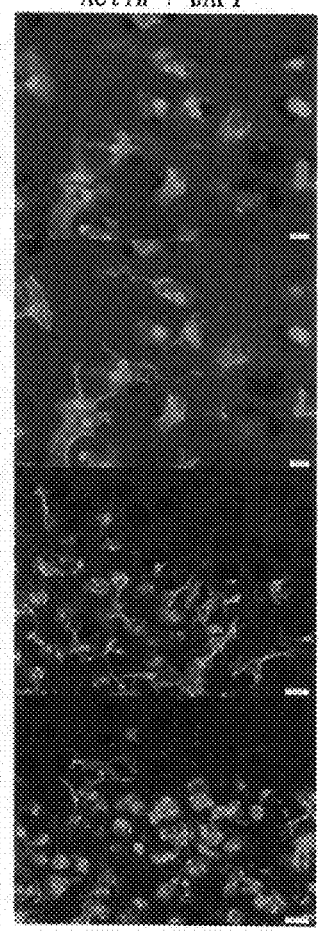

Time-dependent changes in A-surface suction seeding of human mesenchymal stem cells: Single-point wetting method Time-dependent changes during drawn up seeding of human mesenchymal stem cells, according to type of observation surface Low-magnification photographs and experimental observation photographs of human mesenchymal stem cells Stereo microscope | Stereo fluorescent microscope | Material drying and sterilization | Entangled seeding Time-dependent changes during suction seeding of PC12 cells 48hr | Day 4 | Day 6 | Day 9

Results for measurement of cell counts of human skin fibroblasts cultured using porous polyimide film Time-dependent change with natural seeding of human skin keratinocytes Time-dependent change with natural seeding of human umbilical vein endothelial cells Time-dependent change with natural seeding of Vero cells (1) 25μ sheet Time-dependent change with natural seeding of Vero cells (2) 40μ

Time-dependent change with natural seeding of Vero cells (3) 75μ

Time-dependent change with natural seeding of HeLa cells (1) 25μ

Time-dependent change with natural seeding of HeLa cells (2) 40μ

Time-dependent change with natural seeding of HeLa cells (3) 75μ

Time-dependent change with natural seeding of CHO cells (1) 25μ

Time-dependent change with natural seeding of CHO cells (2) 40μ

Time-dependent change with natural seeding of CHO cells (3) 75µ

CELL CULTURING METHOD, CELL CULTURING APPARATUS AND KIT COMPRISING A POROUS POLYIMIDE FILM

This application is a U.S. National Stage Application under 35 U.S.C. §371 of International Patent Application No. PCT/JP2014/070407 filed Jul. 25, 2014, which claims the benefit of priority to Japanese Patent Application No. 2013-155550 filed Jul. 26, 2013, the disclosures of all of which are hereby incorporated by reference in their entireties. The International Application was published in Japanese on Jan. 29, 2015 as WO 2015/012415.

TECHNICAL FIELD

The present invention relates to a cell culturing method, and to a cell culturing apparatus and kit.

BACKGROUND

Cell Culturing

Cells generally exist as three-dimensional aggregates in the body, but in classical plate culturing, cells are cultured in a monolayer fashion with the cells attached to a vessel. Numerous reports have indicated significant differences in cell properties with different culturing environments. An alternative is suspension culturing in which cells are cultured in a liquid culturing medium, but some cells are suited for suspension culture while others are not.

The NanoCulture® Plate (NCP) developed by SCIVAX Corporation is an adhesive-type three-dimensional culturing multiplate patterned with an extracellular matrix (microspheres or microhoneycomb) on the bottom surface by nanoimprint technology. A regular repeating structure is adopted, which is quadrilateral for microspheres and hexagonal for microhoneycombs. The cells utilize this micropattern as a scaffold to actively form spheroids (numerous cells aggregated into a three-dimensional structure).

Also, there have been reports of using cell culture sheets with regular arrangements of numerous uniform superfine cellular projections (nanopillars) ("nanopillar cell culture sheets") for culturing of three-dimensional interstitial tissue (spheroids) having a structure similar to live hepatic tissue (Takahashi et al., Tissue Engineering Part A. June 2012, Vol. 16, No. 6, p. 1983-1995).

Japanese Unexamined Patent Publication No. 2009-213421 describes a spheroid production method and spheroid production apparatus that use a honeycomb-shaped porous film (honeycomb film).

These cell culture methods are similar in that they utilize a sheet (film) having a regular repeating pattern, in that the cells grow while adhering to the sheet surface shape, and in that what are formed by the cell culturing are spheroids in which numerous cells of the same shape are aggregated into a three-dimensional state, and in this sense these methods are restricted. There has been a demand for development of a method for more convenient, more efficient and more stable culturing of cells.

Porous Polyimide Film

Polyimide is a general term for polymers containing imide bonds in the repeating unit, and usually it refers to an aromatic polyimide in which aromatic compounds are directly linked by imide bonds. An aromatic polyimide has an aromatic-aromatic conjugated structure via an imide bond, and therefore has a strong rigid molecular structure, and since imide bonds have powerful intermolecular force, it has a very high level of thermal, mechanical and chemical properties.

Porous polyimide films have been utilized in the prior art for filters, low permittivity films, and especially for battery-related purposes, such as fuel cell electrolyte membranes and the like. International Patent Publication No. WO2010/038873, Japanese Unexamined Patent Publication No. 2011-219585 and Japanese Unexamined Patent Publication No. 2011-219586 describe porous polyimide films with numerous macro-voids, having excellent permeability for gases and the like, high porosity, excellent smoothness on both surfaces, relatively high strength and, despite high porosity, also excellent resistance against compression stress in the film thickness direction.

CITATION LIST

Patent Literature

PTL 1: Japanese Unexamined Patent Publication No. 2009-213421
PTL 2: WO2010/038873
PTL 3: Japanese Unexamined Patent Publication No. 2011-219585
PTL 4: Japanese Unexamined Patent Publication No. 2011-219586

Non-Patent Literature

NPL 1: Takahashi et al., Tissue Engineering Part A. June 2012, Vol. 16, No. 6, p. 1983-1995

DISCLOSURE OF THE INVENTION

Problems to be Solved by the Invention

The present invention relates to a cell culturing method, and to a cell culturing apparatus and kit for use in the culturing method.

Means for Solving the Problems

The present invention preferably includes, but is not limited to, the following modes.
[Mode 1]
A cell culturing method which includes applying cells to a porous polyimide film and culturing them.
[Mode 2]
The method according to mode 1, including a step of seeding cells on the surface of a porous polyimide film.
[Mode 3]
The method according to mode 1, including a step of:
placing a cell suspension on the dried surface of the porous polyimide film,
allowing the porous polyimide film to stand, or moving the porous polyimide film to promote efflux of the liquid, or stimulating part of the surface to cause absorption of the cell suspension into the film, and
retaining the cells in the cell suspension inside the film and allowing the water to flow out.
[Mode 4]
The method according to mode 1, including a step of:
wetting one or both sides of the porous polyimide film with a cell culture medium or a sterilized liquid,
loading a cell suspension into the wetted porous polyimide film, and retaining the cells in the cell suspension inside the film and allowing the water to flow out.

[Mode 5]

The method according to mode 4, wherein the viable cells are retained in the porous polyimide film, and the dead cells are allowed to flow out together with the water.

[Mode 6]

The method according to mode 4 or 5, wherein the sterilized liquid is sterilized water or a sterilized buffering solution.

[Mode 7]

The method according to any one of modes 1 to 6, including the aspect that the cell culture medium, cells and one or more porous polyimide films are placed in a cell culturing vessel, wherein the porous polyimide film is in a suspended state in the cell culture medium.

[Mode 8]

The method according to mode 7, wherein two or more fragments of the porous polyimide film are used.

[Mode 9]

The method according to mode 7 or 8, wherein the cells spontaneously adhere to the porous polyimide film.

[Mode 10]

The method according to any one of modes 1 to 6, wherein the porous polyimide film is:
  i) folded,
  ii) wound into a roll,
  iii) connected as sheets or fragments by a filamentous structure, or
  iv) bound into a rope,
for suspension or fixing in the cell culture medium in the cell culturing vessel.

[Mode 11]

The method according to mode 10, wherein the cells spontaneously adhere to the porous polyimide film.

[Mode 12]

The method according to mode 1, including using two or more porous polyimide films layered either above and below or left and right in the cell culture medium.

[Mode 13]

The method according to mode 1, wherein a combination of two or more of the methods according to modes 2 to 12 is used.

[Mode 14]

The method according to any one of modes 1 to 13, wherein the cells grow and proliferate on the surface of and inside the porous polyimide film.

[Mode 15]

The method according to any one of modes 1 to 14, wherein the cells are selected from the group consisting of animal cells, insect cells, plant cells, yeast cells and bacteria.

[Mode 16]

The method according to mode 15, wherein the animal cells are cells derived from an animal belonging to the subphylum Vertebrata.

[Mode 17]

The method according to mode 15, wherein the bacteria are selected from the group consisting of lactic acid bacteria, *E. coli*, *Bacillus subtilis* and cyanobacteria.

[Mode 18]

The method according to any one of modes 1 to 14, wherein the cells are selected from the group consisting of pluripotent stem cells, tissue stem cells, somatic cells and germ cells.

[Mode 19]

The method according to any one of modes 1 to 13, wherein the cells are selected from the group consisting of sarcoma cells, established cell lines and transformants.

[Mode 20]

The method according to any one of modes 1 to 19, wherein the porous polyimide film is a porous polyimide film including a polyimide obtained from a tetracarboxylic dianhydride and a diamine.

[Mode 21]

A cell culturing apparatus for use in a cell culturing method according to any one of modes 1 to 20, including a porous polyimide film.

[Mode 22]

A cell culturing apparatus according to mode 21, wherein two or more porous polyimide films are layered either above and below or left and right.

[Mode 23]

A kit for use in a cell culturing method according to any one of modes 1 to 20, including a porous polyimide film.

Effect of the Invention

The present invention is based on the finding that when cells are applied to a porous polyimide film, the cells grow. The cells preferably spontaneously adhere to the porous polyimide film, and can grow on the surface and interior of the film. By the method of the invention it has become possible to culture cells in a convenient, efficient and stable manner.

BRIEF DESCRIPTION OF THE DRAWINGS

FIG. 1 shows natural seeding as one mode of seeding of a cell suspension on a porous polyimide film.

FIG. 2 shows suction seeding as one mode of seeding of a cell suspension on a porous polyimide film.

FIG. 3 shows time-dependent change according to type of seeding surface, for natural seeding of human mesenchymal stem cells.

FIG. 4 shows time-dependent change according to type of seeding surface, for natural seeding of human skin fibroblasts.

FIG. 5 shows a fluorescent microscope photograph and a stereomicroscope photograph containing the results of observation with B-surface seeding of human skin fibroblasts (after 24 hours) (wet film method).

FIG. 14-1 shows the results of culturing Vero cells by the method of the present invention using a porous polyimide film (25 µm sheet), by observation under a confocal microscope and a stereo fluorescent microscope.

FIG. 14-2 shows the results of culturing Vero cells by the method of the present invention using a porous polyimide film (40 µm sheet), by observation under a confocal microscope and a stereo fluorescent microscope.

FIG. 14-3 shows the results of culturing Vero cells by the method of the present invention using a porous polyimide film (75 µm sheet), by observation under a confocal microscope and a stereo fluorescent microscope.

FIG. 15-1 shows the results of culturing HeLa cells by the method of the present invention using a porous polyimide film (25 µm sheet), by observation under a confocal microscope and a stereo fluorescent microscope.

FIG. 15-2 shows the results of culturing HeLa cells by the method of the present invention using a porous polyimide film (40 µm sheet), by observation under a confocal microscope and a stereo fluorescent microscope.

FIG. 15-3 shows the results of culturing HeLa cells by the method of the present invention using a porous polyimide film (75 µm sheet), by observation under a confocal microscope and a stereo fluorescent microscope.

FIG. 16-1 shows the results of culturing CHO cells by the method of the present invention using a porous polyimide film (25 µm sheet), by observation under a confocal microscope and a stereo fluorescent microscope.

FIG. 16-2 shows the results of culturing CHO cells by the method of the present invention using a porous polyimide film (40 µm sheet), by observation under a confocal microscope and a stereo fluorescent microscope.

FIG. 16-3 shows the results of culturing CHO cells by the method of the present invention using a porous polyimide film (75 µm sheet), by observation under a confocal microscope and a stereo fluorescent microscope.

MODE FOR CARRYING OUT THE INVENTION

I. Cell Culturing Method

Figure 6:
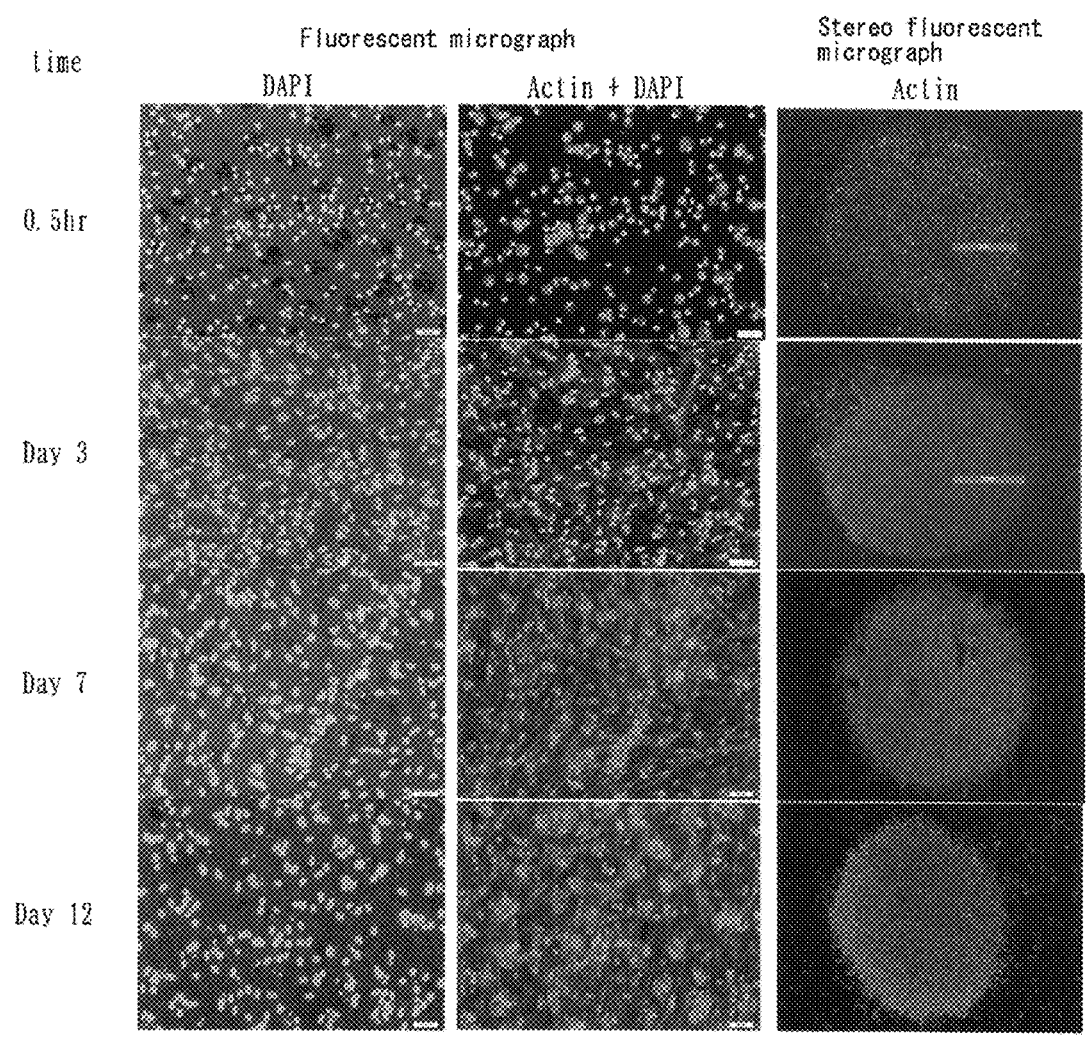
FIG. 6 shows time-dependent changes with A-surface suction seeding of human mesenchymal stem cells (single-point wetting method).

The present invention relates to a cell culturing method.

The cell culturing method of the invention includes applying cells to a porous polyimide film and culturing them. The present inventors have found that a porous polyimide film is suitable for adhesion and culturing of cells, and have thereupon completed this invention. The method of the invention includes applying cells to a porous polyimide film and culturing the cells on the surface or in the interior of the polyimide film.

Application of Cells to Porous Polyimide Film

There are no particular restrictions on the specific steps for application of the cells to the porous polyimide film. It is possible to carry out the steps described throughout the present specification, or to employ any desired method suited for applying cells to a film-like support. The method of the invention includes, but is not limited to, the following modes.

(A) A mode including a step of seeding cells on the surface of the porous polyimide film;

(B) A mode including a step of placing a cell suspension on the dried surface of the porous polyimide film, allowing it to stand, or moving the porous polyimide film to promote efflux of the liquid, or stimulating part of the surface to cause absorption of the cell suspension into the film, and retaining the cells in the cell suspension inside the film and allowing the water to flow out; and (C) A mode including a step of wetting one or both sides of the porous polyimide film with a cell culture medium solution or a sterilized liquid, loading a cell suspension into the wetted porous polyimide film, and retaining the cells in the cell suspension inside the film and allowing the water to flow out.

Mode (A) includes a step of directly seeding cells or a cell mass on the surface of a porous polyimide film. Alternatively, it includes a mode of placing a porous polyimide film in a cell suspension and wetting the cell culture solution from the surface of the film.

Cells seeded on the surface of a porous polyimide film adhere to the porous polyimide film and infiltrate into the interiors of the pores. Preferably, the cells adhere spontaneously to the porous polyimide film without applying any particular exterior physical or chemical force. The cells that have been seeded on the surface of the porous polyimide film can stably grow and proliferate on the surface and/or in the interior of the film. The cells may be in a variety of different forms, depending on the location of the film used for growth and proliferation.

For mode (B), a cell suspension is placed on the dried surface of a porous polyimide film. The porous polyimide film is allowed to stand, or the porous polyimide film is moved to promote efflux of the liquid, or part of the surface is stimulated to cause absorption of the cell suspension into the film, so that the cell suspension permeates into the film. While it is not our intention to be constrained by theory, this is believed to be due to the properties of each surface forms of the porous polyimide film. According to this mode, the cells are absorbed and seeded in the locations of the film where the cell suspension has been loaded.

Alternatively, as according to mode (C), after all or a portion of one or both sides of the porous polyimide film has been wetted with the cell culture solution or sterilized liquid, the cell suspension may be loaded into the wetted porous polyimide film. This will significantly increase the transit rate of the cell suspension.

For example, the single-point wetting method described in Example 4 of the present specification is a method of wetting a portion of the film edges for the main purpose of preventing fly loss of the film, and it is nearly the same as the dry method (mode (B)) in which the film is not essentially wetted. However, it is possible that cell solution permeation through the film is more rapid at the small wetted portions. Also, the wet film method described in Example 3 of the present specification is a method in which all of one or both sides of the porous polyimide film that have been thoroughly wetted (hereunder this will also be referred to as "wet film") is loaded with a cell suspension. In this case, the entire porous polyimide film has a greatly increased transit rate for the cell suspension.

According to modes (B) and (C), the cells in the cell suspension are retained in the film, while the water flows out. This allows treatment such as increasing the concentration of cells in the cell suspension and flowing out of unwanted non-cellular components together with the water.

Mode (A) will also be referred to as "natural seeding", and modes (B) and (C) as "suction seeding".

Preferably, but not restrictively, the viable cells are selectively retained in the porous polyimide film. Thus, according to a preferred mode of the invention, the viable cells are retained in the porous polyimide film, and the dead cells preferentially flow out together with the water. In Example 3 of the invention, the viable cell rate was 90% in the cell culture medium (cell suspension) before application to the porous polyimide film of the invention, but the viable cell rate was 65% in the liquid efflux after application to the porous polyimide film. Compared in terms of cell viability, for viable cells, the adsorption rate into the film was 88% and the efflux rate was 12%, while for dead cells, the adsorption rate into the film was 40% and the efflux rate was 60%. This is interpreted as that viable cells are selectively adsorbed into the porous polyimide film of the invention.

The sterilized liquid used for mode (C) is not particularly restricted, and may be a sterilized buffering solution or sterilized water. A buffering solution may be, for example, (+) or (−) Dulbecco's PBS, or (+) or (−) Hank's Balanced Salt Solution. Examples of buffering solutions are listed in Table 1 below.

TABLE 1

| Component | Concentration (mmol/L) | Concentration (g/L) |
| --- | --- | --- |
| NaCl | 137 | 8.00 |
| KCl | 2.7 | 0.20 |
| $Na_2HPO_4$ | 10 | 1.44 |
| $KH_2PO_4$ | 1.76 | 0.24 |
| pH (−) | 7.4 | 7.4 |

The invention further includes a mode of adding adhesive cells in a floating (suspended) state as a suspension together with a porous polyimide film, to adhere the cells with the film (entangling). For example, for application of the cells to the porous polyimide film in the cell culturing method of the invention, the cell culture medium, the cells and one or more of the porous polyimide films may be placed in the cell culturing vessel. When the cell culture medium is a liquid, the porous polyimide film is in a floating (suspended) state in the cell culture medium. The cells can adhere to the porous polyimide film due to the properties of the porous polyimide film. Thus, even with cells that are not suited for natural suspension culture, the porous polyimide film allows culturing in a floating state in the cell culture medium. The cells preferably spontaneously adhere to the porous polyimide film. Here, "adhere spontaneously" means that the cells are retained on the surface or in the interior of the porous polyimide film without applying any particular exterior physical or chemical force.

Cell culturing can be classified into culturing where the cultured cells are adhesion culture-type cells or suspension culture-type cells, depending on the state in the cell culture. Adhesion culture-type cells are cultured cells that adhere and grow on a culturing vessel, with the medium being exchanged at the time of subculture. Suspension culture-type cells are cultured cells that grow in a suspended state in a medium, and generally the medium is not exchanged at the time of subculture but dilution culture is carried out. Because suspension culture allows culturing in a suspended state, i.e. in a liquid, mass culturing becomes possible, and because it is three-dimensional culturing, unlike with adhering cells that grow only on the culturing vessel surface, the advantage of increased culturable cell count per unit space is afforded.

According to the invention, in conceptual terms, there is provided a method in which it is possible to grow cells in a form similar to suspension culture without being limited to the cell type, so that cells can be conveniently cultured in large amounts. According to the cell culture method of the invention, when the porous polyimide film is used in a state suspended in the cell culture medium, two or more fragments of the porous polyimide film may be used. Since the porous polyimide film is a flexible thin-film, using such fragments that are suspended in the culture solution, for example, allows a porous polyimide film with a large surface area to be added into a fixed volume of cell culture medium. In the case of normal culturing, the container base area constitutes the area limit in which cell culture can be accomplished, but with cell culturing using the porous polyimide film of the invention, all of the large surface area of the previously added porous polyimide film constitutes area in which cell culturing can be accomplished. The porous polyimide film allows the cell culture solution to pass through, allowing supply of nutrients, oxygen and the like even into the folded film, for example.

The sizes and shapes of the porous polyimide film fragments are not particularly restricted. The shapes may be as desired, such as circular, elliptical, quadrilateral, triangular, polygonal or string-like. This includes, for example, quadrilaterals (square, rectangular or the like) and triangular shapes with side lengths of about 0.1 mm to about 20 mm, preferably about 0.2 mm to about 10 mm and more preferably about 1 mm to about 5 mm. Alternatively, for example, they may be circular, with diameters of preferably about 0.1 mm to about 20 mm and more preferably about 0.5 mm to about 10 mm. Dispersing the fragments in the liquid results in a form similar to a suspension culture.

Because the porous polyimide film of the invention is flexible, it can be used with varying shapes. Instead of a flat form, the porous polyimide film can also be used by working into a three-dimensional shape. For example, the porous polyimide film may be: i) folded, ii) wound into a roll, iii) connected as sheets or fragments by a filamentous structure, or iv) bound into a rope, for suspension or fixing in the cell culture medium in the cell culturing vessel. By forming it into shapes such as i) to iv), it is possible to place a large amount of porous polyimide film into a fixed volume of cell culture medium, similar to using fragments. Furthermore, since each fragment can be treated as an aggregate, it is possible to aggregate and move the cell masses, for overall high applicability.

With the same concept as fragment aggregates, two or more porous polyimide films may be used in a layered form either above and below or left and right in the cell culture medium. Layering includes a mode in which portions of the porous polyimide films overlap. Layered culturing allows culturing of cells at high density in a narrow space. It is also possible to further layer a film on a film on which cells are already growing, setting it to create a multilayer of different cell types. This may also be used for drug development, including verification of intercellular interaction in a three-dimensional environment, or in a non-stress cell culture method. The number of layered porous polyimide films is not particularly restricted.

Two or even more forms of the cell culturing method of the invention described above may be used in combination. For example, using any of the methods of modes (A) to (C), first the cells may be applied to the porous polyimide film and then the cell-adhered porous polyimide film may be used for suspension culture. Alternatively, the step of application to the porous polyimide film may be a combination of two or more of the methods of any of modes (A) to (C).

In the method of the invention, preferably the cells grow and proliferate on the surface or in the interior of the porous polyimide film. No reports exist disclosing growth and proliferation of cells inside a three-dimensional structure. By utilization of a porous polyimide film according to the invention it is possible to accomplish continuous three-dimensional culturing of cells. While not restrictive, the method of the invention carries out continuous growth of cells for 2 days or longer, more preferably 4 days or longer and even more preferably 6 days or longer. In Examples 1 and 4 described in the present specification, growth of cells was observed for 21 days.

2. Cells

There are no particular restrictions on the type of cells that can be utilized for the method of the invention, and it may be used for growth of any type of cells.

For example, the cells may be selected from the group consisting of animal cells, insect cells, plant cells, yeast cells and bacteria. Animal cells are largely divided into cells from animals belonging to the subphylum Vertebrata, and cells from non-vertebrates (animals other than animals belonging to the subphylum Vertebrata). There are no particular restrictions on the source of the animal cells, for the purpose of the present specification. Preferably, they are cells from an animal belonging to the subphylum Vertebrata. The subphylum Vertebrata includes the superclass Agnatha and the superclass Gnathostomata, the superclass Gnathostomata including the class Mammalia, the class Aves, the class Amphibia and the class Reptilia. Preferably, they are cells from an animal belonging to the class Mammalia, generally known as mammals. Mammals are not particularly restricted but include, preferably, mice, rats, humans, monkeys, pigs, dogs, sheep and goats.

There are also no particular restrictions on sources of plant cells, for the purpose of the present specification. Suitable cells are from plants including bryophytes, pteridophytes and spermatophytes.

Plants from which spermatophyte cells are derived include both monocotyledons and dicotyledons. While not restrictive, monocotyledons include Orchidaceae plants, Poaceae plants (rice, corn, barley, wheat, sorghum and the like) and Cyperaceae plants. Dicotyledons include plants belonging to many subclasses including the subclass Chrysanthemum, the subclass Magnoliidae and the subclass Rosidae.

Algae may be considered cell-derived organisms. These include different groups, from the eubacteria Cyanobacteria (blue-green algae), to eukaryotic monocellular organisms (diatoms, yellow-green algae, dinoflagellates and the like) and multicellular marine algae (red algae, brown algae and green algae).

There are no particular limitations on the types of archaebacteria or bacteria for the purpose of the present specification. Archaebacteria are composed of groups comprising methanogenic bacteria, extreme halophilic bacteria, thermophilic acidophilic bacteria, hyperthermophilic bacteria and the like. Bacteria are selected from the group consisting of, for example, lactic acid bacteria, *E. coli, Bacillus subtilis* and cyanobacteria.

The types of animal cells or plant cells that may be used for the method of the invention are not particularly restricted, but are preferably selected from the group consisting of pluripotent stem cells, tissue stem cells, somatic cells and germ cells.

The term "pluripotent stem cells", for the purpose of the invention, is intended as a comprehensive term for stem cells having the ability to differentiate into cells of a variety of tissues (pluripotent differentiating power). While not restrictive, pluripotent stem cells include embryonic stem cells (ES cells), induced pluripotent stem cells (iPS cells), embryonic germ cells (EG cells) and germ stem cells (GS cells). They are preferably ES cells or iPS cells. Particularly preferred are iPS cells, which are free of ethical problems, for example. The pluripotent stem cells used may be any publicly known ones, and for example, the pluripotent stem cells described in International Patent Publication No. WO2009/123349 (PCT/JP2009/057041) may be used.

The term "tissue stem cells" refers to stem cells that are cells lines capable of differentiation but only to limited specific tissues, though having the ability to differentiate into a variety of cell types (pluripotent differentiating power). For example, hematopoietic stem cells in the bone marrow are the source of blood cells, while neural stem cells differentiate into neurons. Additional types include hepatic stem cells from which the liver is formed and skin stem cells that form skin tissue. Preferably, the tissue stem cells are selected from among mesenchymal stem cells, hepatic stem cells, pancreatic stem cells, neural stem cells, skin stem cells and hematopoietic stem cells.

The term "somatic cells" refers to cells other than germ cells, among the cells composing a multicellular organism. With sexual reproduction, these are not passed on to the next generation. Preferably, the somatic cells are selected from among hepatocytes, pancreatic cells, muscle cells, bone cells, osteoblasts, osteoclasts, chondrocytes, adipocytes, skin cells, fibroblasts, pancreatic cells, renal cells and lung cells, or blood cells such as lymphocytes, erythrocytes, leukocytes, monocytes, macrophages or megakaryocytes.

The term "germ cells" refers to cells having the role of passing on genetic information to the succeeding generation in reproduction. These include, for example, gametes for sexual reproduction, i.e. the ova, egg cells, sperm, sperm cells, and spores for asexual reproduction.

The cells may also be selected from the group consisting of sarcoma cells, established cell lines and transformants. The term "sarcoma" refers to cancer occurring in non-epithelial cell-derived connective tissue cells, such as the bone, cartilage, fat, muscle or blood, and includes soft sarcomas, malignant bone tumors and the like. Sarcoma cells are cells derived from sarcoma. The term "established cell line" refers to cultured cells that are maintained in vitro for long periods and reach a stabilized character and can be semi-permanently subcultured. Cell lines derived from various tissues of various species including humans exist, such as PC12 cells (from rat adrenal medulla), CHO cells (from Chinese hamster ovary), HEK293 cells (from human embryonic kidney), HL-60 cells (from human leukocytes) and HeLa cells (from human cervical cancer). The term "transformants" refers to cells with an altered genetic nature by extracellularly introduced nucleic acid (DNA and the like). Suitable methods are known for transformation of animal cells, plant cells and bacteria.

3. Porous Polyimide Film

Polyimide is a general term for polymers containing imide bonds in the repeating unit, and usually it refers to an aromatic polyimide in which aromatic compounds are directly linked by imide bonds. An aromatic polyimide has an aromatic-aromatic conjugated structure via an imide bond, and therefore has a strong rigid molecular structure, and since imide bonds have powerful intermolecular force, it has very high levels of thermal, mechanical and chemical properties.

The porous polyimide film of the invention is preferably a porous polyimide film including (as the main component) a polyimide obtained from a tetracarboxylic dianhydride and a diamine, and more preferably it is a porous polyimide film comprising a polyimide obtained from a tetracarboxylic dianhydride and a diamine. The phrase "including as the main component" means that it essentially contains no components other than the polyimide obtained from a tetracarboxylic dianhydride and a diamine, as constituent components of the porous polyimide film, or that it may contain them but they are additional components that do not affect the properties of the polyimide obtained from the tetracarboxylic dianhydride and diamine.

This also includes colored porous polyimide films obtained by forming a polyamic acid solution composition containing a polyamic acid solution obtained from a tetracarboxylic acid component and a diamine component, and a coloring precursor, and then heat treating it at 250° C. or higher.

Polyamic Acid

A polyamic acid is obtained by polymerization of a tetracarboxylic acid component and a diamine component. A polyamic acid is a polyimide precursor that can be cyclized to a polyimide by thermal imidization or chemical imidization.

The polyamic acid used may be any one that does not have an effect on the invention, even if a portion of the amic acid is imidized. Specifically, the polyamic acid may be partially thermally imidized or chemically imidized.

When the polyamic acid is to be thermally imidized, there may be added to the polyamic acid solution, if necessary, an imidization catalyst, an organic phosphorus-containing compound, or fine particles such as inorganic fine particles or organic fine particles. Also, when the polyamic acid is to be chemically imidized, there may be added to the polyamic acid solution, if necessary, a chemical imidization agent, a dehydrating agent, or fine particles such as inorganic fine particles or organic fine particles. Even if such components are added to the polyamic acid solution, they are preferably added under conditions that do not cause precipitation of the coloring precursor.

Coloring Precursor

For the purpose of the invention, a coloring precursor is a precursor that generates a colored substance by partial or total carbonization under heat treatment at 250° C. or higher.

Coloring precursors to be used for the invention are preferably uniformly dissolved or dispersed in a polyamic acid solution or polyimide solution and subjected to thermal decomposition by heat treatment at 250° C. or higher, preferably 260° C. or higher, even more preferably 280° C. or higher and more preferably 300° C. or higher, and preferably heat treatment in the presence of oxygen such as air, at 250° C., preferably 260° C. or higher, even more preferably 280° C. or higher and more preferably 300° C. or higher, for carbonization to produce a colored substance, more preferably producing a black colored substance, with carbon-based coloring precursors being most preferred.

The coloring precursor, when heating, first appears as a carbonized compound, but compositionally it contains other elements in addition to carbon, and also includes layered structures, aromatic crosslinked structures and tetrahedron carbon-containing disordered structures.

Carbon-based coloring precursors are not particularly restricted, and for example, these include tar or pitch such as petroleum tar, petroleum pitch, coal tar and coal pitch, coke, polymers obtained from acrylonitrile-containing monomers, ferrocene compounds (ferrocene and ferrocene derivatives), and the like. Of these, polymers obtained from acrylonitrile-containing monomers and/or ferrocene compounds are preferred, with polyacrylnitrile being preferred as a polymer obtained from an acrylonitrile-containing monomer.

The tetracarboxylic dianhydride used may be any tetracarboxylic dianhydride, selected as appropriate according to the properties desired. Specific examples of tetracarboxylic dianhydrides include biphenyltetracarboxylic dianhydrides such as pyromellitic dianhydride, 3,3',4,4'-biphenyltetracarboxylic dianhydride (s-BPDA) and 2,3,3',4'-biphenyltetracarboxylic dianhydride (a-BPDA), oxydiphthalic dianhydride, diphenylsulfone-3,4,3',4'-tetracarboxylic dianhydride, bis(3,4-dicarboxyphenyl)sulfide dianhydride, 2,2-bis(3,4-dicarboxyphenyl)-1,1,1,3,3,3-hexafluoropropane dianhydride, 2,3,3',4'-benzophenonetetracarboxylic dianhydride, 3,3',4,4'-benzophenonetetracarboxylic dianhydride, bis(3,4-dicarboxyphenyl)methane dianhydride, 2,2-bis(3,4-dicarboxyphenyl)propane dianhydride, p-phenylenebis(trimellitic acid monoester acid anhydride), p-biphenylenebis (trimellitic acid monoester acid anhydride), m-terphenyl-3, 4,3',4'-tetracarboxylic dianhydride, p-terphenyl-3,4,3',4'-tetracarboxylic dianhydride, 1,3-bis(3,4-dicarboxyphenoxy) benzene dianhydride, 1,4-bis(3,4-dicarboxyphenoxy) benzene dianhydride, 1,4-bis(3,4-dicarboxyphenoxy) biphenyl dianhydride, 2,2-bis[(3,4-dicarboxyphenoxy) phenyl]propane dianhydride, 2,3,6,7-naphthalenetetracarboxylic dianhydride, 1,4,5,8-naphthalenetetracarboxylic dianhydride, 4,4'-(2,2-hexafluoroisopropylidene)diphthalic dianhydride, and the like. Also preferably used is an aromatic tetracarboxylic acid such as 2,3,3',4'-diphenylsulfonetetracarboxylic acid. These may be used alone or in appropriate combinations of two or more.

Particularly preferred among these are at least one type of aromatic tetracarboxylic dianhydride selected from the group consisting of biphenyltetracarboxylic dianhydride and pyromellitic acid dianhydride. As a biphenyltetracarboxylic dianhydride there may be suitably used 3,3',4,4'-biphenyltetracarboxylic dianhydride.

Any desired diamine may be used as a diamine. Specific examples of diamines include the following.

1) Benzenediamines with one benzene nucleus, such as 1,4-diaminobenzene(paraphenylenediamine), 1,3-diaminobenzene, 2,4-diaminotoluene and 2,6-diaminotoluene;

2) diamines with two benzene nuclei, including diaminodiphenyl ethers such as 4,4'-diaminodiphenyl ether and 3,4'-diaminodiphenyl ether, and 4,4'-diaminodiphenylmethane, 3,3'-dimethyl-4,4'-diaminobiphenyl, 2,2'-dimethyl-4,4'-diaminobiphenyl, 2,2'-bis(trifluoromethyl)-4,4'-diaminobiphenyl, 3,3'-dimethyl-4,4'-diaminodiphenylmethane, 3,3'-dicarboxy-4,4'-diaminodiphenylmethane, 3,3',5,5'-tetramethyl-4,4'-diaminodiphenylmethane, bis(4-aminophenyl)sulfide, 4,4'-diaminobenzanilide, 3,3'-dichlorobenzidine, 3,3'-dimethylbenzidine, 2,2'-dimethylbenzidine, 3,3'-dimethoxybenzidine, 2,2'-dimethoxybenzidine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenylsulfone, 3,4'-diaminodiphenylsulfone, 4,4'-diaminodiphenylsulfone, 3,3'-diaminobenzophenone, 3,3'-diamino-4,4'-dichlorobenzophenone, 3,3'-diamino-4,4'- dimethoxybenzophenone, 3,3'-diaminodiphenylmethane, 3,4'-diaminodiphenylmethane, 4,4'-diaminodiphenylmethane, 2,2-bis(3-aminophenyl)propane, 2,2-bis(4-aminophenyl)propane, 2,2-bis(3-aminophenyl)-1,1,1,3,3,3-hexafluoropropane, 2,2-bis(4-aminophenyl)-1,1,1,3,3,3-hexafluoropropane, 3,3'-diaminodiphenyl sulfoxide, 3,4'-diaminodiphenyl sulfoxide and 4,4'-diaminodiphenyl sulfoxide;

3) diamines with three benzene nuclei, including 1,3-bis (3-aminophenyl)benzene, 1,3-bis(4-aminophenyl)benzene, 1,4-bis(3-aminophenyl)benzene, 1,4-bis(4-aminophenyl) benzene, 1,3-bis(4-aminophenoxy)benzene, 1,4-bis(3-aminophenoxy)benzene, 1,4-bis(4-aminophenoxy)benzene, 1,3-bis(3-aminophenoxy)-4-trifluoromethylbenzene, 3,3'-diamino-4-(4-phenyl)phenoxybenzophenone, 3,3'-diamino-4,4'-di(4-phenylphenoxy)benzophenone, 1,3-bis(3-aminophenyl sulfide)benzene, 1,3-bis(4-aminophenyl sulfide) benzene, 1,4-bis(4-aminophenyl sulfide)benzene, 1,3-bis(3-aminophenylsulfone)benzene, 1,3-bis(4-aminophenylsulfone)benzene, 1,4-bis(4-aminophenylsulfone)benzene, 1,3-bis[2-(4-aminophenyl) isopropyl]benzene, 1,4-bis[2-(3-aminophenyl)isopropyl] benzene and 1,4-bis[2-(4-aminophenyl)isopropyl]benzene;

4) diamines with four benzene nuclei, including 3,3'-bis (3-aminophenoxy)biphenyl, 3,3'-bis(4-aminophenoxy)biphenyl, 4,4'-bis(3-aminophenoxy)biphenyl, 4,4'-bis(4-aminophenoxy)biphenyl, bis[3-(3-aminophenoxy) phenyl] ether, bis[3-(4-aminophenoxy)phenyl]ether, bis[4-(3-aminophenoxy)phenyl]ether, bis[4-(4-aminophenoxy) phenyl]ether, bis[3-(3-aminophenoxy)phenyl]ketone, bis[3-(4-aminophenoxy)phenyl]ketone, bis[4-(3-aminophenoxy) phenyl]ketone, bis[4-(4-aminophenoxy)phenyl]ketone, bis [3-(3-aminophenoxy)phenyl] sulfide, bis[3-(4-aminophenoxy)phenyl] sulfide, bis[4-(3-aminophenoxy) phenyl] sulfide, bis[4-(4-aminophenoxy)phenyl] sulfide, bis[3-(3-aminophenoxy)phenyl]sulfone, bis[3-(4-aminophenoxy) phenyl]sulfone, bis[4-(3-aminophenoxy) phenyl]sulfone, bis[4-(4-aminophenoxy)phenyl]sulfone, bis[3-(3-aminophenoxy)phenyl]methane, bis[3-(4-aminophenoxy)phenyl] methane, bis[4-(3-aminophenoxy) phenyl]methane, bis[4-(4-aminophenoxy)phenyl]methane, 2,2-bis[3-(3-aminophenoxy)phenyl]propane, 2,2-bis[3-(4-aminophenoxy)phenyl]propane, 2,2-bis[4-(3-aminophenoxy) phenyl]propane, 2,2-bis[4-(4-aminophenoxy)phenyl]propane, 2,2-bis[3-(3-aminophenoxy)phenyl]-1,1,1,3,3,3-hexafluoropropane, 2,2-bis[3-(4-aminophenoxy)phenyl]-1,1,1,3,3,3-hexafluoropropane, 2,2-bis[4-(3-aminophenoxy) phenyl]-1,1,1,3,3,3-hexafluoropropane and 2,2-bis[4-(4-aminophenoxy)phenyl]-1,1,1,3,3,3-hexafluoropropane.

These may be used alone or in mixtures of two or more. The diamine used may be appropriately selected according to the properties desired.

Preferred among these are aromatic diamine compounds, with 3,3'-diaminodiphenyl ether, 3,4'-diaminodiphenyl ether, 4,4'-diaminodiphenyl ether, paraphenylenediamine, 1,3-bis(3-aminophenyl)benzene, 1,3-bis(4-aminophenyl) benzene, 1,4-bis(3-aminophenyl)benzene, 1,4-bis(4-aminophenyl)benzene, 1,3-bis(4-aminophenoxy) benzene and 1,4-bis(3-aminophenoxy)benzene being preferred for use. Particularly preferred is at least one type of diamine selected from the group consisting of benzenediamines, diaminodiphenyl ethers and bis (aminophenoxy)phenyl.

From the viewpoint of heat resistance and dimensional stability under high temperature, the porous polyimide film is preferably formed from a polyimide obtained by combination of a tetracarboxylic dianhydride and a diamine, having a glass transition temperature of 240° C. or higher, or without a distinct transition point at 300° C. or higher.

From the viewpoint of heat resistance and dimensional stability under high temperature, the porous polyimide film of the invention is preferably a porous polyimide film comprising one of the following aromatic polyimides.

(i) An aromatic polyimide comprising at least one tetracarboxylic acid unit selected from the group consisting of biphenyltetracarboxylic acid units and pyromellitic acid units, and an aromatic diamine unit, (ii) an aromatic polyimide comprising a tetracarboxylic acid unit and at least one type of aromatic diamine unit selected from the group consisting of benzenediamine units, diaminodiphenyl ether units and bis(aminophenoxy)phenyl units, and/or, (iii) an aromatic polyimide comprising at least one type of tetracarboxylic acid unit selected from the group consisting of biphenyltetracarboxylic acid units and pyromellitic acid units, and at least one type of aromatic diamine unit selected from the group consisting of benzenediamine units, diaminodiphenyl ether units and bis(aminophenoxy)phenyl units.

While not restrictive, the porous polyimide film for use in the method of the invention may be a porous polyimide film with a multilayer structure, having at least two surface layers (A-surface and B-surface), and a macro-void layer sandwiched between the two surface layers. Preferably, the porous polyimide film is a porous polyimide film wherein the macro-void layer has a partition bonded to the surface layers (A-surface and B-surface) and a plurality of macro-void with mean pore sizes of 10 to 500 μm in the planar direction of the film, surrounded by the partition and the surface layers (A-surface and B-surface), wherein the macro-void layer partition and the surface layers (A-surface and B-surface) each have thicknesses of 0.01 to 20 μm, with a plurality of pores with mean pore sizes of 0.01 to 100 μm, the pores being optionally communicating with each other, and also having a partial or total multilayer structure in communication with the macro-void, where the total film thickness is 5 to 500 μm and the porosity is 40% or greater and less than 95%.

The total film thickness is not restricted but may be 25 to 75 μm according to one mode. Differences in the film thickness may be observed as differences in cell growth rate, cell morphology, cell saturation within the plate, and the like.

According to one mode, the A-surface of the porous polyimide film is a mesh structure having small holes with mean sizes of no greater than 15 μm, and the B-surface is a large-hole structure with mean sizes of 20 μm or greater.

For example, the porous polyimide films described in International Patent Publication No. WO2010/038873, Japanese Unexamined Patent Publication No. 2011-219585 and Japanese Unexamined Patent Publication No. 2011-219586 may also be used in the method of the invention.

The cells that have been seeded on the surface of the porous polyimide film can stably grow and proliferate on the surface and/or in the interior of the film. The cells may be in a variety of different forms, depending on the location of growth and proliferation in the film. According to one mode of the invention, growth may be carried out while moving the surface and interior of the porous polyimide film and changing the form, depending on the type of cell.

4. Cell Culturing Method and Cell Culture Medium

For the method of the invention, after the cells have been applied to the porous polyimide film, the cells may be cultured using any known method. Culturing methods suited for various cells including animal cells, plant cells and bacteria are publicly known, and a person skilled in the art may carry out culturing of cells on the porous polyimide film using any publicly known method. The cell culture medium may also be prepared as appropriate for the type of cells.

Cell culture methods and cell culture media for animal cells may be found in the Cell Culture Media Catalog of Lonza Group, Ltd., for example. Cell culture methods and cell culture media for plant cells may be found in the Plant Tissue Culturing Media Series by Wako Corp., for example. Cell culture methods and cell culture media for bacteria may be found in the General Bacterial Media Catalog of BD Corp., for example.

II. Cell Culturing Apparatus

The present invention also relates to a cell culturing apparatus for use in the culturing method of the invention, the apparatus including a porous polyimide film. In the cell culturing apparatus of the invention, the porous polyimide film may be used in a fixed state, or it may be used in a floating state in the cell culture medium. In the cell culturing apparatus, two or more porous polyimide films may be layered either above and below or left and right.

The cell culturing apparatus used for the invention may be a publicly known cell culturing apparatus so long as it satisfies the condition of including a porous polyimide film. The shape and scale of the culturing apparatus is not particularly restricted, and any scale from a dish or test tube to a large tank may be used, as appropriate. These include, for example, Cell Culture Dish by BD Falcon, and Nunc Cell Factory by Thermo Scientific. By using a porous polyimide film according to the invention, it has become possible to carry out culturing even of cells that have not been capable of natural suspension culture, using an apparatus intended for suspension culture, in a state similar to suspension culturing. The apparatus for suspension culture that is used may be, for example, a spinner flask by Corning, Inc.

III. Kit for Use in Cell Culturing Method

The present invention also relates to a kit for use in the cell culturing method of the invention, the apparatus including a porous polyimide film.

The kit of the invention may include constituent elements necessary for cell culturing in addition to the porous polyimide film, as appropriate. This includes, for example, the cells applied to the porous polyimide film, the cell culture medium and the instruction manual for the cell culturing apparatus and the kit.

While not restrictive, one mode includes a package containing either one or a plurality of sterilized porous polyimide films stored in a transparent pouch, in a form allowing their use for cell culturing, or a kit having sterile liquid encapsulated together with a porous polyimide film in the same pouch, in the form of an integrated film/liquid allowing efficient suction seeding.

EXAMPLES

The present invention will now be explained in detail by examples, with the understanding that these examples are in no way limitative on the invention. A person skilled in the art may easily implement modifications and changes to the invention based on the description in the present specification, and these are also encompassed within the technical scope of the invention. Unless otherwise specified, "porous polyimide film" refers to a porous polyimide film with a film thickness of 25 µm.

Example 1: Natural Seeding of Human Mesenchymal Stem Cells in Porous Polyimide Film For this example, human mesenchymal stem cells were used for seeding in a porous polyimide film.

After adding 0.5 ml of cell culture medium to a 2 cm×2 cm sterilized square vessel, a sterilized 1.4 cm-square porous polyimide film was dipped therein with the A-surface of the mesh structure or the B-surface of the large-gap structure facing upward. Separately, there was prepared a human mesenchymal stem cell suspension, with human mesenchymal stem cells suspended at $3.6\times10^5$ per 1 ml of medium (of which viable cells were $3.4\times10^5$ and dead cells were $2.0\times10^4$, for a viable cell rate of 94%). Each cell suspension was added at 60 µl to the cell culture medium in the square vessel.

After culturing in a cell culturing apparatus for 1 hour, 5 hours, 24 hours, 48 hours, 4 days, 7 days, 14 days and 21 days, the cells were fixed and stained (DAPI, or actin+DAPI), and the cell growth and proliferation were confirmed. The actin staining was done with phalloidin. The cell proliferation and seeding surface-specific form over time were observed. The results are shown in FIG. 3. These results indicated that human mesenchymal stem cells, a typical type of stem cell, can also be cultured by the method of the present invention.

Example 2: Natural Seeding of Human Skin Fibroblasts in Porous Polyimide Film For this example, human skin fibroblasts were used, applying the cells to the porous polyimide film by natural seeding.

After adding 0.5 ml of cell culture medium to a 2 cm×2 cm sterilized square vessel, a sterilized 1.4 cm-square porous polyimide film was dipped therein with the A-surface of the mesh structure or the B-surface of the large-gap structure facing upward. Separately, there was prepared a human skin fibroblast suspension with human skin fibroblasts suspended at $8.3\times10^5$ per 1 ml of medium (of which viable cells were $8.1\times10^5$ and dead cells were $2.0\times10^4$, for a viable cell rate of 98%). Each cell suspension was added at 50 µl to the cell culture medium in the square vessel.

After culturing in a cell culturing apparatus for 1 hour, 5 hours, 24 hours, 48 hours, 4 days, 7 days, 14 days and 21 days, the cells were fixed and stained (DAPI, or actin+DAPI), and the cell growth and proliferation were confirmed. Proliferation of the cells over time and the seeding surface-specific and observation surface-specific forms were observed. The results are shown in FIG. 4. These results indicated that human skin fibroblasts, a typical type of fibroblast, can also be cultured by the method of the present invention.

Example 3: Suction Seeding of Human Skin Fibroblasts in Porous Polyimide Film (Wet Film Method)

For this example, human skin fibroblasts were used, applying the cells to the porous polyimide film by suction seeding onto a wet film (a thoroughly wetted film; details are described below).

There was prepared a human skin fibroblast suspension with the cells suspended at $1.0 \times 10^6$ per 1 ml of medium (of which viable cells were $9.1 \times 10^5$ and dead cells were $1.0 \times 10^5$, for a viable cell rate of 90%). On a 10 cm×14 cm rectilinear plate there were aligned, without overlapping, 25 1.4 cm-square porous polyimide films wetted with 1 ml of cell culture medium, and 20 µl of cell suspension was added to the B-surface of each porous polyimide film. The exuded liquid was drained, each porous polyimide film was transferred to a 75 cm² dish, and 12 ml of medium was added. Culturing was then carried out under ordinary conditions, and the specimen was fixed on the following day. FIG. 5 shows a fluorescent microscope photograph and a stereo fluorescent microscope photograph of a fixed and fluorescent-stained (DAPI or actin+DAPI) specimen after 24 hours.

During the seeding step, the exuded liquid was recovered, the rectilinear plate was further rinsed with 2 ml of medium and the cells remaining on the plate were counted, resulting in a total cell count of $6.0 \times 10^4$, of which $5.5 \times 10^4$ were viable cells and $3.0 \times 10^4$ were dead cells, for a viable cell rate of 65%. Compared in terms of cell viability, for the viable cells, the adsorption rate into the film was 88% and the efflux rate was 12%, while for the dead cells, the adsorption rate into the film was 40% and the efflux rate was 60%.

Example 4: Suction Seeding of Human Mesenchymal Stem Cells in Porous Polyimide Film (Single-Point Wetting Method)

For this example, human mesenchymal stem cells were used, applying the cells to the porous polyimide film by suction seeding onto a single-point wetted film (a simple fixed film wetted at only the center point with a liquid droplets; details are described below).

For this example, human mesenchymal stem cells were used, applying the cells to the porous polyimide film by suction seeding onto a film wetted only at the center point of the film material.

At the center section where the film was to be placed, a droplet of about 10 µl was formed and the porous polyimide film was placed over it, attempting to fix the film area to create an easily seedable location, while utilizing the moisture to increase the rapidity of cell solution film permeation.

Figure 7:
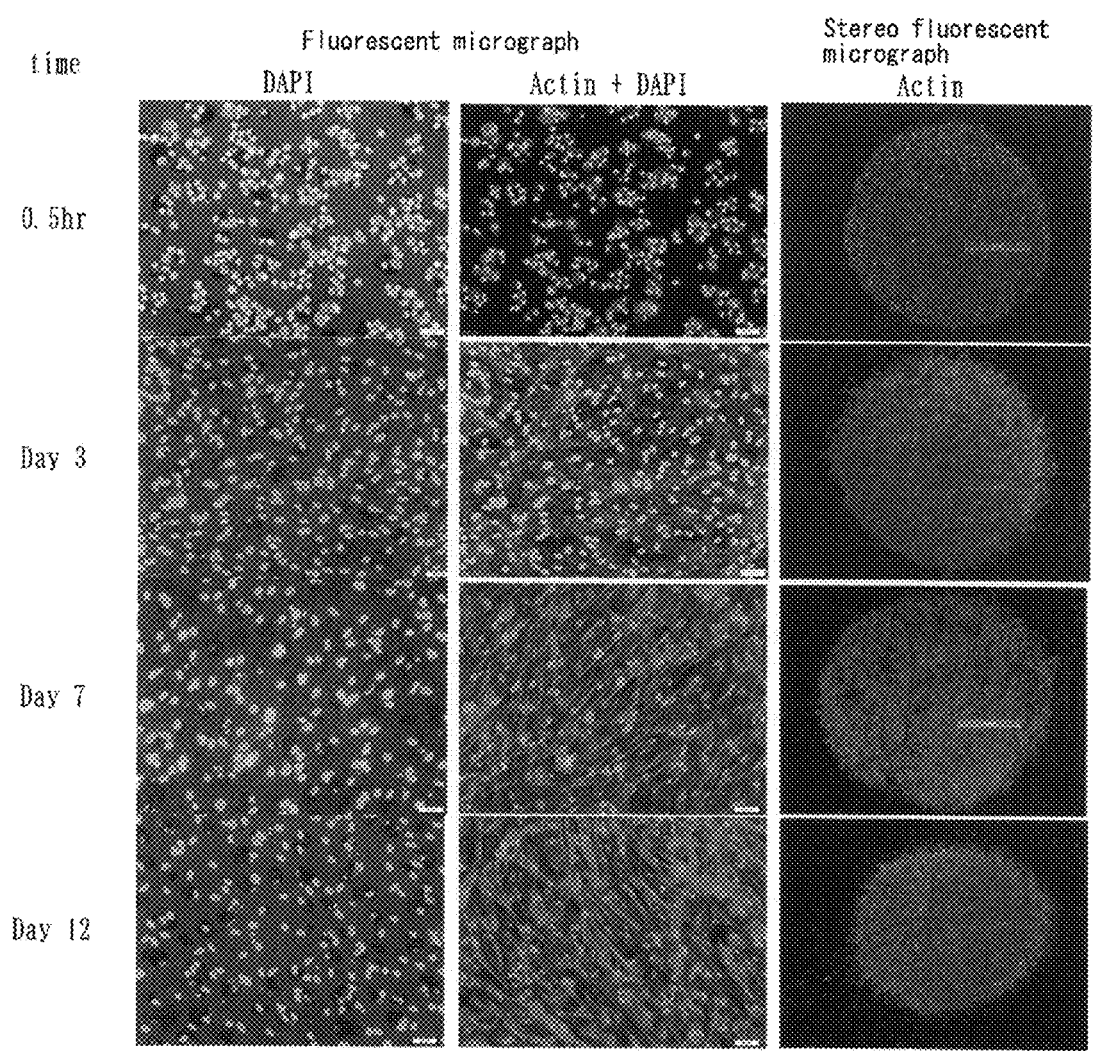
FIG. 7 shows time-dependent changes with B-surface suction seeding of human mesenchymal stem cells (single-point wetting method).

There was prepared a human mesenchymal stem cell suspension with the cells suspended at $1.0 \times 10^6$ per 1 ml of medium (of which viable cells were $9.6 \times 10^5$ and dead cells were $4.0 \times 10^4$, for a viable cell rate of 96%). On a 10 cm×14 cm rectilinear plate there were aligned, without overlapping, 10 sterilized and dried 1.4 cm-square porous polyimide films on their A-surfaces and B-surfaces, and 40 µl of cell suspension was added to each porous polyimide film. The exuded liquid was drained, the porous polyimide film was transferred to a 10 cm² dish for each seeding surface, and 2 ml of medium was added. Culturing was then carried out under ordinary culturing conditions, the cells were fixed and stained (DAPI, actin+DAPI or actin) after 0.5 hour, 3 days, 7 days and 12 days and the cell growth and proliferation were confirmed. The results are shown in FIG. 6 and FIG. 7.

During the seeding step, the exuded liquid was recovered, the rectilinear plate was further rinsed with 4 ml of medium and the cells remaining on the plate were counted, resulting in a total cell count of $6.5 \times 10^4$, with A-surface seeding, of which $4.0 \times 10^4$ were viable cells and $2.5 \times 10^4$ were dead cells, for a viable cell rate of 62%. Compared in terms of cell viability, for the viable cells, the adsorption rate into the film was 89% and the efflux rate was 11%, while for the dead cells, presumably efflux occurred essentially without adsorption. With B-surface seeding, the total cell count was $6.5 \times 10^4$, of which $8.0 \times 10^4$ were viable cells and $2.0 \times 10^4$ were dead cells, for a viable cell rate of 80%. Compared in terms of cell viability, for the viable cells, the adsorption rate into the film was 79% and the efflux rate was 21%, while for the dead cells, presumably efflux occurred essentially without adsorption.

Example 5: Entangled Seeding of Human Mesenchymal Stem Cells in Porous Polyimide Film For this example, human mesenchymal stem cells were used, applying the cells to the porous polyimide film by drawing up of the cell suspension.

Figure 8:
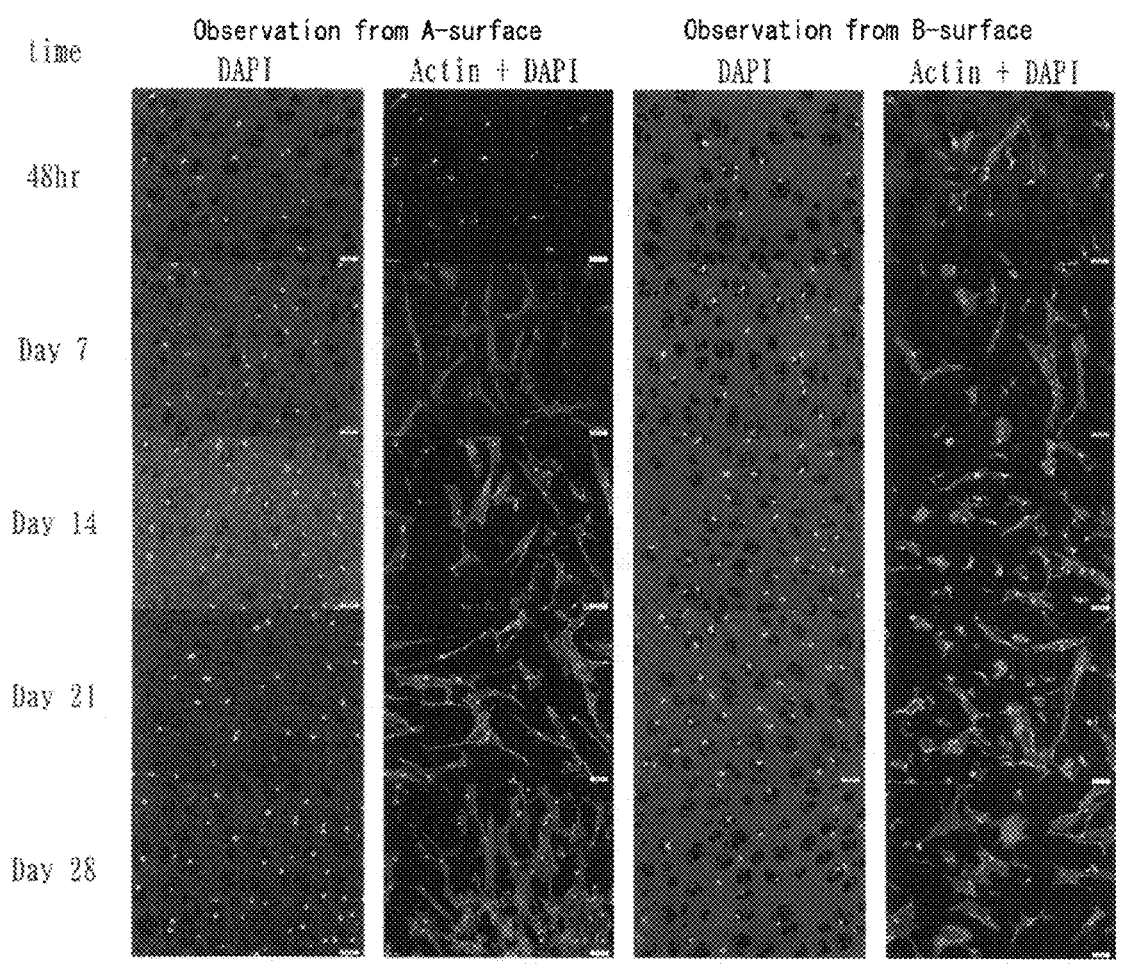
FIG. 8 shows time-dependent change according to type of observation surface, for entangled seeding of human mesenchymal stem cells.
Figure 9:
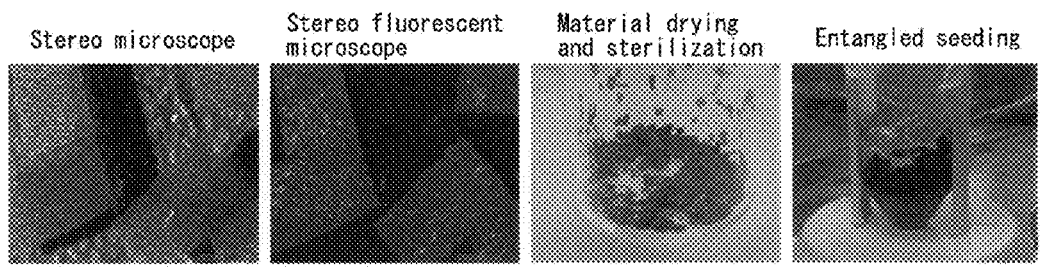
FIG. 9 shows low-magnification photographs and experimental results photographs for entangled seeding of human mesenchymal stem cells.

A square porous polyimide film with 10 cm sides was cut into approximately 2 to 3 mm square fragments using scissors, and after sterilization at 160° C. for 10 minutes, the fragments were allowed to cool and wetted with 2 ml of sterilized medium. Next, the porous polyimide film was cut with forceps and transferred to a Falcon tube. To the film in the Falcon tube there were added 1.6 ml of a human mesenchymal stem cell suspension, obtained by suspending cells at $3.6 \times 10^5$ per 1 ml of medium (of which viable cells were $3.4 \times 10^5$ and dead cells were $2.0 \times 10^4$, for a viable cell rate of 94%) (total cell count: $5.7 \times 10^5$, of which $5.4 \times 10^5$ were viable cells and $3.2 \times 10^4$ were dead cells). These were allowed to stand for 2 hours in the culturing vessel with periodic shaking, and upon measuring the cell count in the liquid portion, there were observed $2.0 \times 10^5$ cells (of which $1.2 \times 10^5$ were viable cells and $8.0 \times 10^4$ were dead cells, for a viable cell rate of 60%). The porous polyimide film fragments were cut out and transferred to a 20 cm² dish spread with 4 ml of medium, and subcultured in a culturing vessel. The fragments were fixed and stained after 48 hours, 7 days, 14 days, 21 days and 28 days (DAPI or actin+DAPI), and the cell growth and proliferation were observed. The results are shown in FIG. 8 and FIG. 9.

Example 6: Suction Seeding of Established Cell Line in Porous Polyimide Film Fragments For this example, cells of the established cell line PC12 were used, applying the cells to porous polyimide film fragments by suction seeding.

On a 10 cm×14 cm rectilinear plate, 15 1.4 cm-square porous polyimide films previously wetted with 5 ml of medium and having the liquid thoroughly removed, were aligned in a random fashion with partially overlapping portions above and below and left and right. Separately, there was prepared a cell suspension of rat adrenal pheochromocytoma PC12 cells, with the cells suspended at $9.0 \times 10^5$ per 1 ml of medium (of which viable cells were $7.4 \times 10^5$ and dead cells were $1.7 \times 10^5$, for a viable cell rate of 82%). A 2 ml portion of the cell suspension was slowly added to the film while slightly tilting the plate to cause the exudated liquid to move downward. After 5 minutes, the exudated liquid was drained from the porous polyimide film and transfered to 4 ml of medium spread onto a previously prepared 20 cm² dish, and culturing was carried out in a culturing apparatus.

Figure 10:
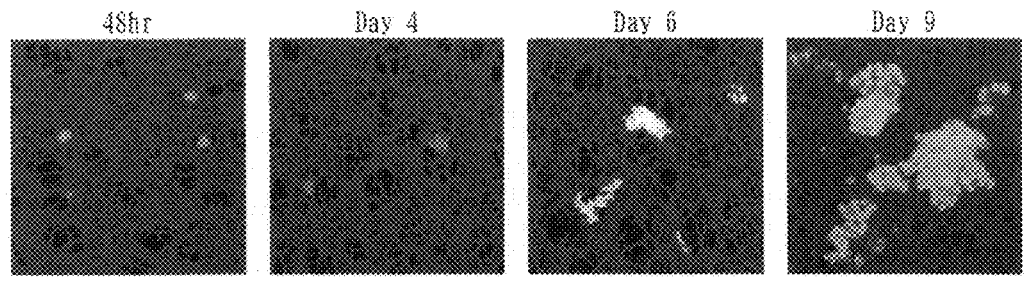
FIG. 10 shows time-dependent changes during suction seeding of PC12 cells.

After 48 hours, 4 days, 6 days and 9 days, the porous polyimide film was fixed and stained, and proliferation of the cells was confirmed. The staining was performed with a membrane fluorescence stain cell mask (CellMask™ Orange plasma membrane stain (Life Technologies), hereunder also referred to simply as "CellMask")+DAPI. The results are shown in FIG. 10. With these cells as well, there was observed a state of proliferation while forming aggregates inside the porous polyimide film, thereby confirming their applicability. The results indicated that PC12 cells, a typical type of established cell line, can also be cultured by the method of the present invention.

Example 7: Measurement of Cultured Cell Count

For this example, human skin fibroblasts were cultured by the method of the invention using a porous polyimide film, and the cultured cell count was measured.
1. Cell Count Measurement of Ordinary Cultured Cells Using CCK8

First, the following reagent and method were used to calculate the cell count with ordinary culturing, and the correlation coefficient between the absorbance and actual cell count was determined.
[Reagent] Cell Counting Kit 8; Dojindo, Solution reagent (hereunder referred to as "CCK8").
[Method] Human skin fibroblasts cultured on a 5 cm² chamber dish for a prescribed period were prepared, the culture supernatant was removed, exchange was performed with a fixed amount of medium containing CCK8 added at 2%, and the cells were kept in an incubator for 2 hours. Next, the colored supernatant was extracted and the absorbance at a wavelength of 480 nm was measured (the blank used being conditions of measurement with the medium alone). After then removing the supernatant, the cells were rinsed twice with phosphate buffer and treated with 0.05% trypsin-EDTA solution, and the cell count was determined.

The correlation coefficient between absorbance and actual cell count was determined for the culturing conditions and CCK8 concentration conditions by this method.
2. Measurement of Cell Count Proliferated on Porous Polyimide Film As in 1. above, a cell-cultured 2 cm² (1.4 cm×1.4 cm) porous polyimide film was transferred to a 5 cm² chamber dish, a fixed amount of 5% CCK8-added medium was added, and the film was kept in an incubator for 1 to 3 hours, after which the supernatant was extracted and the absorbance at a wavelength of 480 nm was measured. In this case, the CCK8 was used in a 2.5-fold amount, whereas in terms of area, the porous polyimide film area was only an area of 2.5 times smaller, and therefore a direct comparison can be made with the values read in 1. (When the concentration, area or other conditions have been changed, a conversion is necessary.) The conversion coefficient determined in 1. is used to calculate the surviving cell count on the material, and then rinsing is performed twice with medium, and after returning to the incubator, culturing is continued. This procedure was repeated, and the state of proliferation of the cells on the porous polyimide film was periodically analyzed in a quantitative manner. Reproducibility was verified by conducting several experiments.

Figure 11:
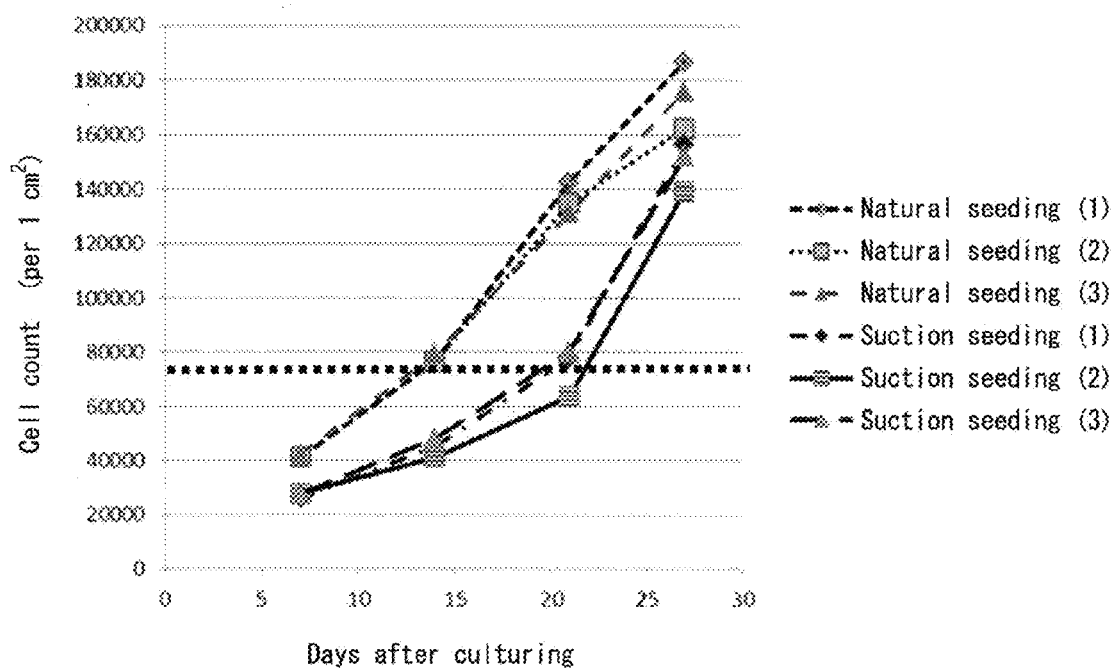
FIG. 11 shows cell counts for human skin fibroblasts cultured using a porous polyimide film with a film thickness of 25 μm. The abscissa represents number of days after culturing, and the ordinate represents the cell count per square centimeter of film.

The results for natural seeding and suction seeding, each conducted 3 times, are shown in FIG. 11. As shown in FIG. 11, the cell proliferation rate differs depending on the method of seeding, but the difference disappears with about 1 month of culturing, reaching similar cell counts per unit area. The dotted lines in the graph indicate the upper limit for the cultured cell count for ordinary adhesive culturing in a dish, carried out as a comparative experiment. When the cell counts were compared based on area, it was found to be possible to culture a larger amount of cells in a unit area compared to ordinary cell culturing.

Example 8: Culturing of Human Skin Keratinocytes

For this example, human skin keratinocytes were cultured by the method of the present invention using a porous polyimide film, and observed under a confocal microscope and a stereo fluorescent microscope.

After adding 0.5 ml of cell culture medium (KGM-Gold keratinocyte growth medium, BulletKit (product of Lonza Group, Ltd.)) to a 2 cm×2 cm sterilized square vessel, a sterilized 1.4 cm-square porous polyimide film was dipped therein with the A-surface of the mesh structure facing upward. Human skin keratinocytes were added in an amount of $4\times10^4$ to the cell culture medium in the square vessel. Specifically, $4\times10^4$ human skin keratinocytes were naturally seeded for each 1.4 cm-square porous polyimide film.

Culturing was carried out in a cell culturing apparatus, and the cells were fixed and stained after 1 day, 3 days and 6 days. The staining was accomplished with CellMask+ DAPI or with CellMask alone. Next, a confocal microscope (LSM700 (product of Carl Zeiss)) and a stereo fluorescent microscope (Leica M165 FC (product of Leica Microsystems GmbH)) were used for periodic observation of the proliferation and form of the cells.

Figure 12:
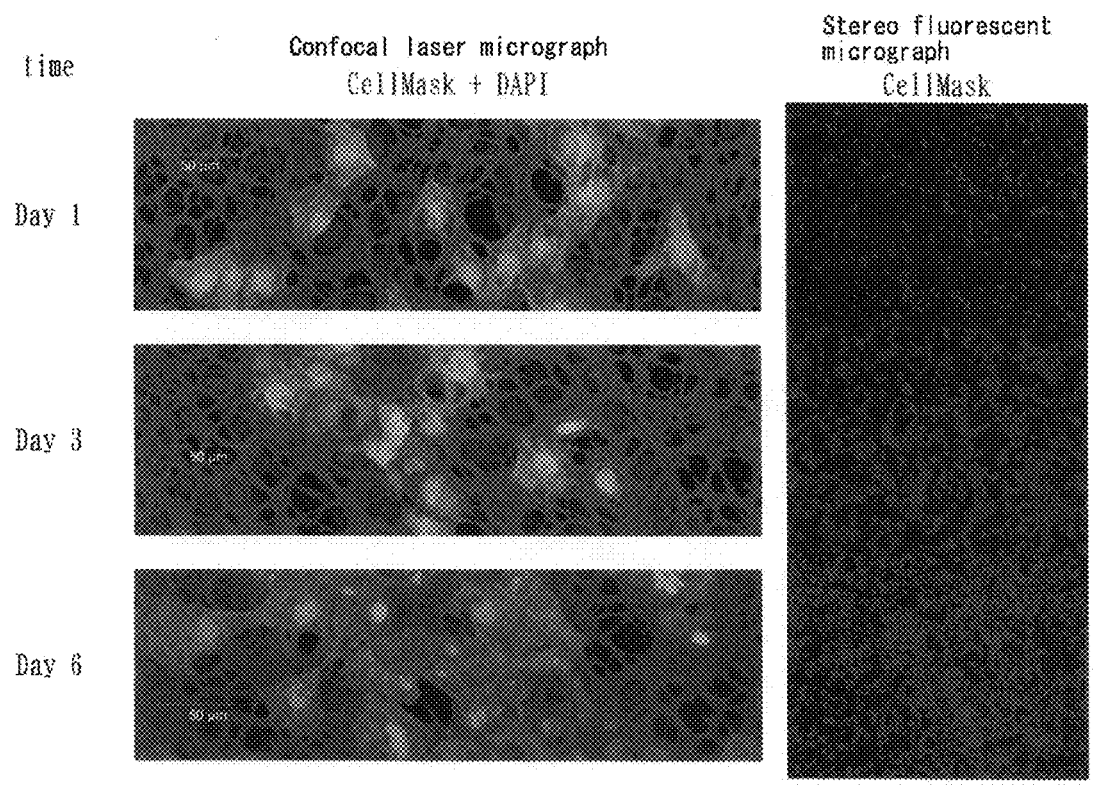
FIG. 12 shows the results of culturing human skin keratinocytes by the method of the present invention using a porous polyimide film, by observation under a confocal microscope and a stereo fluorescent microscope.

The results are shown in FIG. 12. The results indicated that human skin keratinocytes, as human primary cultured cells, can also be cultured by the method of the invention.

Example 9: Culturing of Human Umbilical Vein Endothelial Cells

For this example, human umbilical vein endothelial cells were cultured by the method of the present invention using a porous polyimide film, and observed under a confocal microscope and a stereo fluorescent microscope.

After adding 0.5 ml of cell culture medium (EGM-2 BulletKit (product of Lonza Group, Ltd.)) to a 2 cm×2 cm sterilized square vessel, a sterilized 1.4 cm-square porous polyimide film was dipped therein with the A-surface of the mesh structure facing upward. Human umbilical vein endothelial cells were added in an amount of $4\times10^4$ to the cell culture medium in the square vessel. Specifically, $4\times10^4$ human umbilical vein endothelial cells were naturally seeded for each 1.4 cm-square porous polyimide film.

Culturing was carried out in a cell culturing apparatus, and the cells were fixed and stained (CellMask+DAPI and CellMask) after 3 days, 6 days and 10 days. Staining and observation under a confocal microscope and a stereo fluorescent microscope were carried out in the same manner as Example 8.

Figure 13:
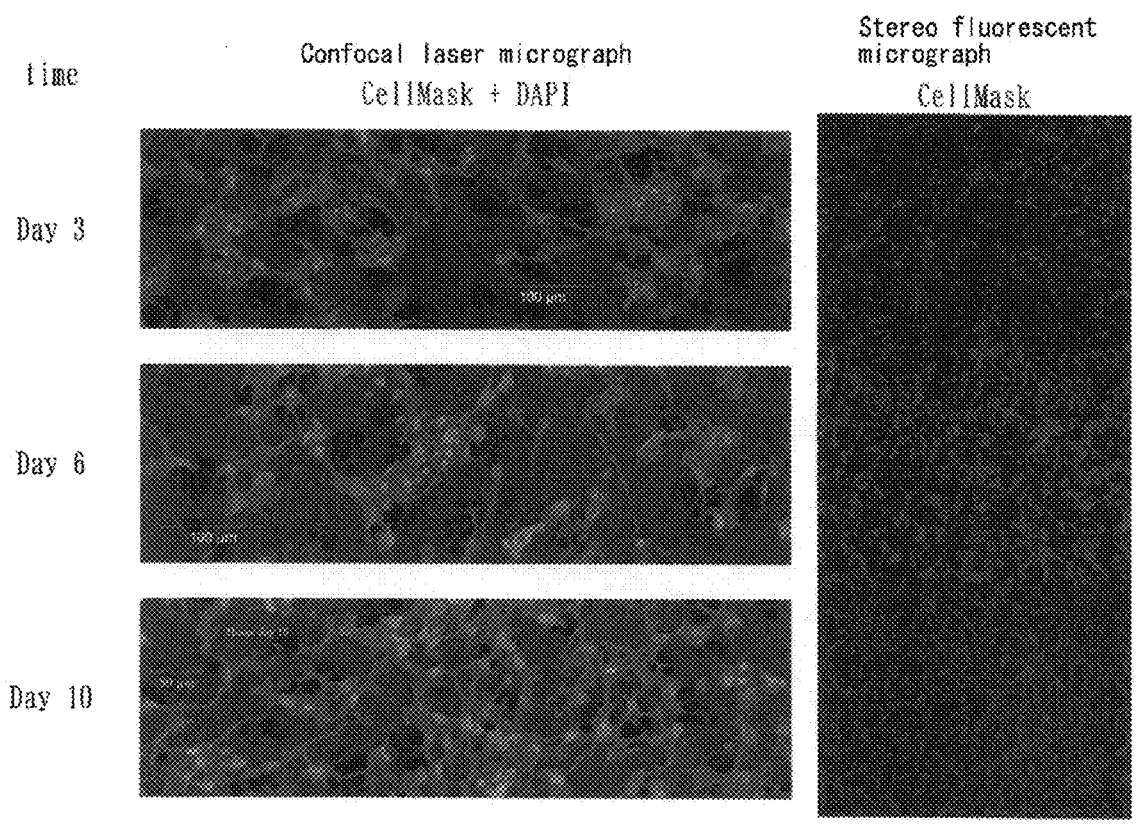
FIG. 13 shows the results of culturing human umbilical vein endothelial cells by the method of the present invention using a porous polyimide film, by observation under a confocal microscope and a stereo fluorescent microscope.

The results are shown in FIG. 13. The results indicated that human umbilical vein endothelial cells, as human primary cultured cells, can also be cultured by the method of the invention.

Example 10: Culturing of Vero Cells

For this example, Vero cells were cultured by the method of the present invention using a porous polyimide film, and observed under a confocal microscope and a stereo fluorescent microscope. The porous polyimide films used were of the three types: 25 μm, 40 μm and 75 μm. The culturing period was 1 to 15 days.

After adding 0.5 ml of cell culture medium (mixture of 10% FBS and an antibiotic added to DMEM) to a 2 cm×2 cm sterilized square vessel, a sterilized 1.4 cm-square porous polyimide film was dipped therein with the A-surface of the mesh structure facing upward. Vero cells were added in an amount of $4\times10^4$ to the cell culture medium in the square vessel. That is, $4\times10^4$ Vero cells were naturally seeded for each 1.4 cm-square porous polyimide film.

Culturing was carried out in a cell culturing apparatus, and the cells were fixed and stained after 1 day, 3 days, 7 days, 10 days and 15 days. The staining was accomplished with actin+DAPI, and actin detection was with phalloidin. Observation under a confocal microscope and a stereo fluorescent microscope were carried out in the same manner as Example 8.

Figures 1, 14:
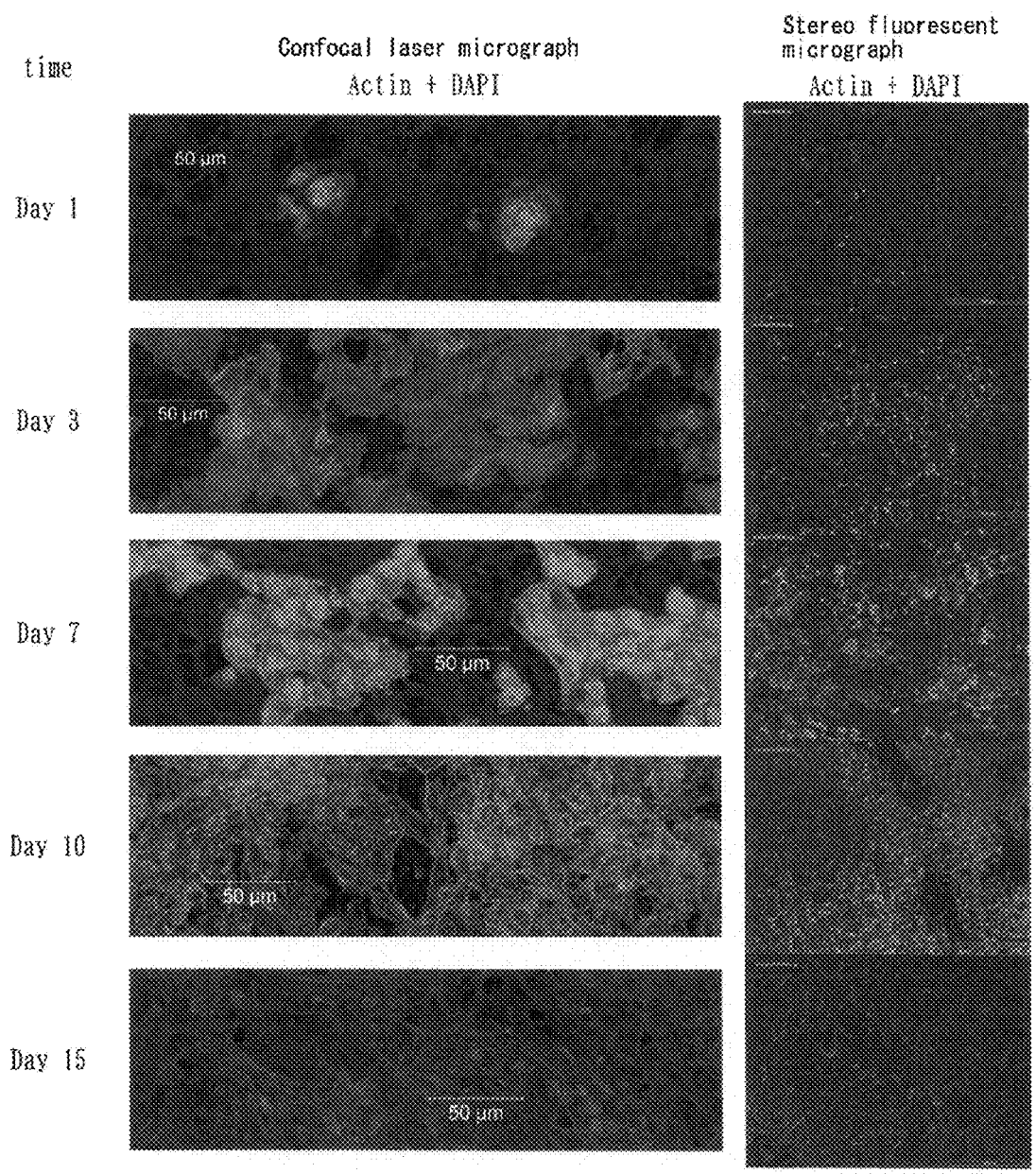
Figures 2, 14:
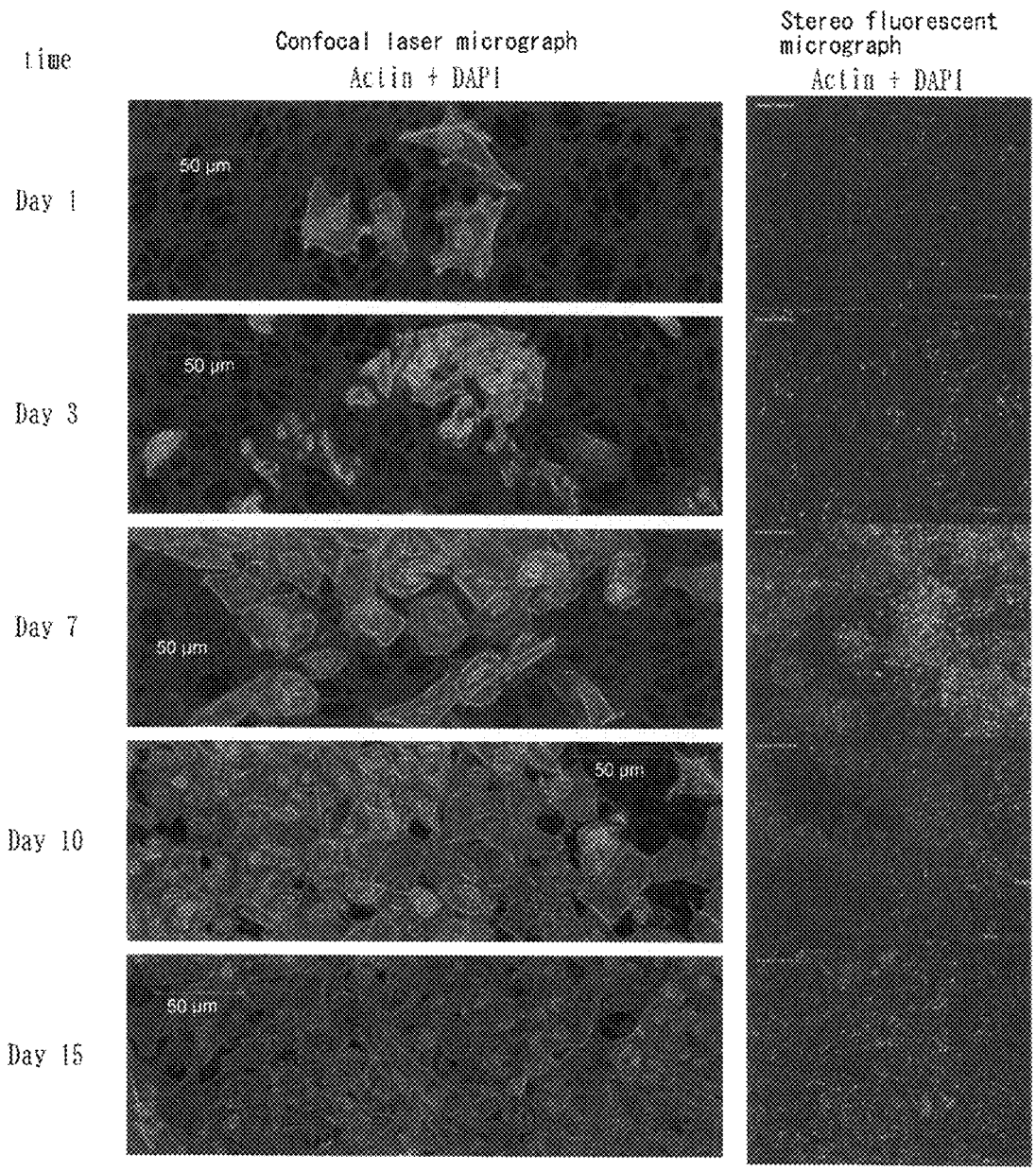
Figures 3, 14:
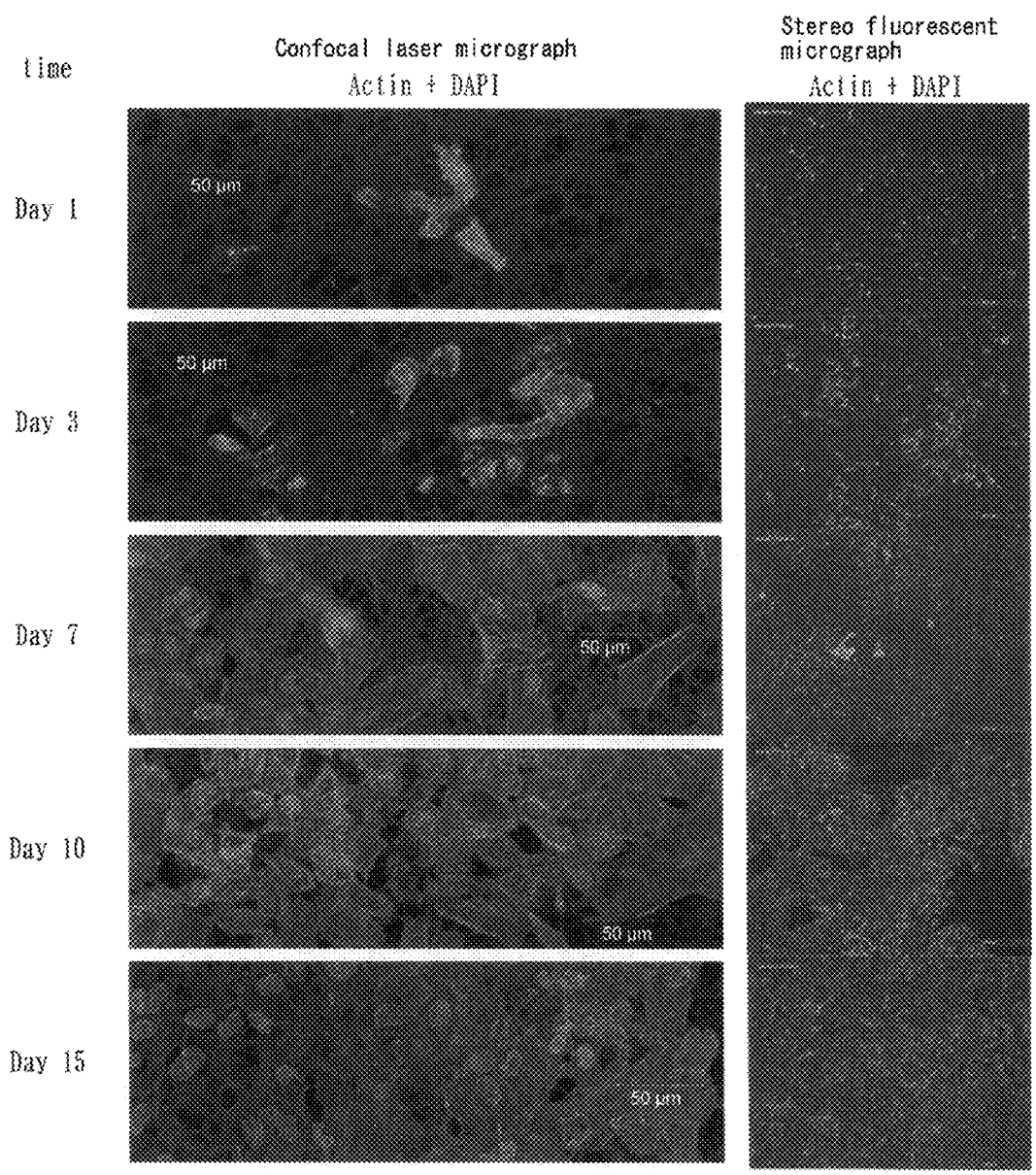

The results are shown in FIGS. 14-1 to 14-3. The results indicated that Vero cells, a typical type of established cell line, can also be cultured by the method of the present invention.

Example 11: Culturing of HeLa Cells

For this example, HeLa cells were cultured by the method of the present invention using a porous polyimide film, and observed under a confocal microscope and a stereo fluorescent microscope. The porous polyimide films used were of the three types: 25 μm, 40 μm and 75 μm. The culturing period, microscopes used and specific steps were as described in Example 10.

Figures 1, 15:
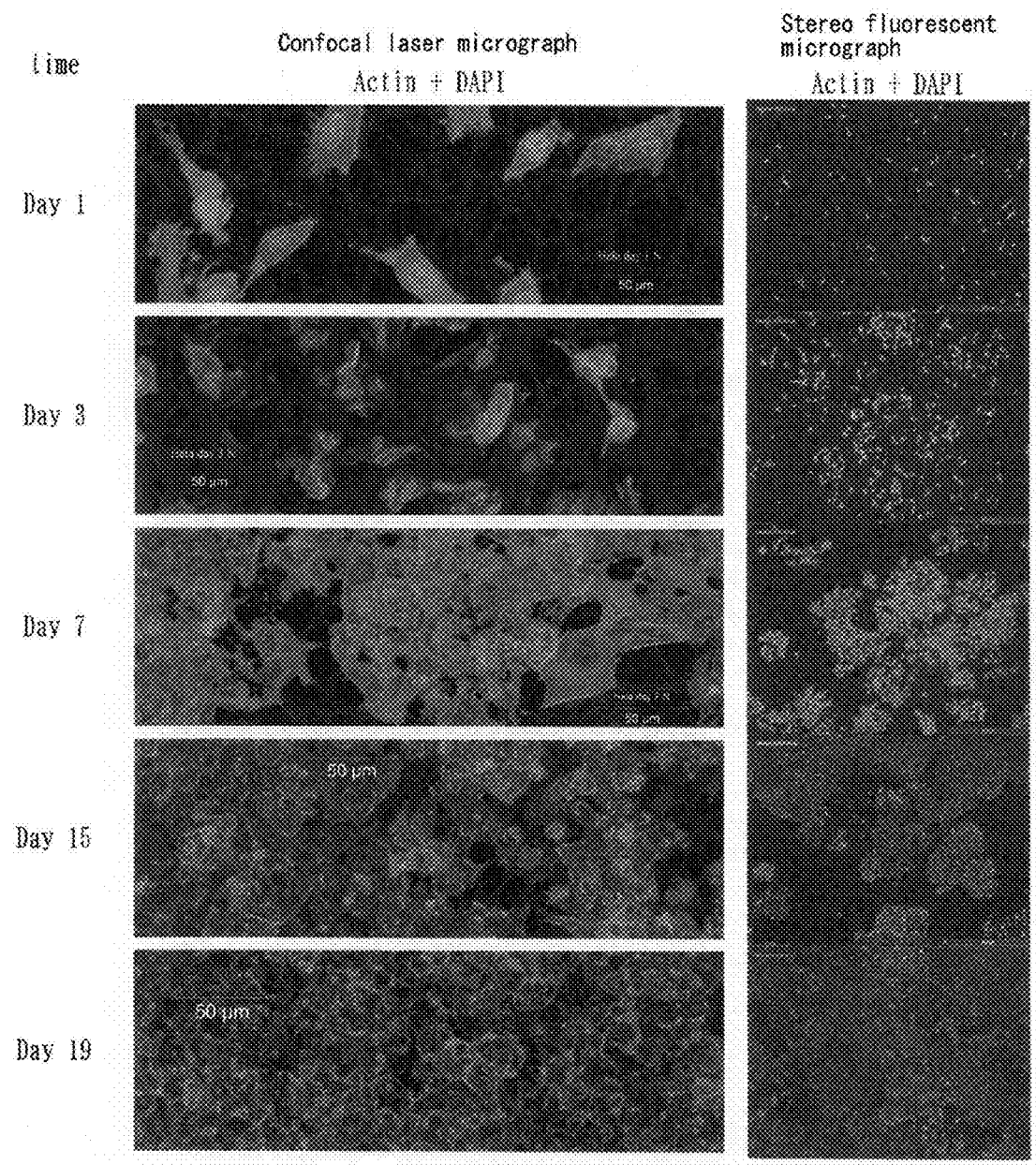
Figures 2, 15:
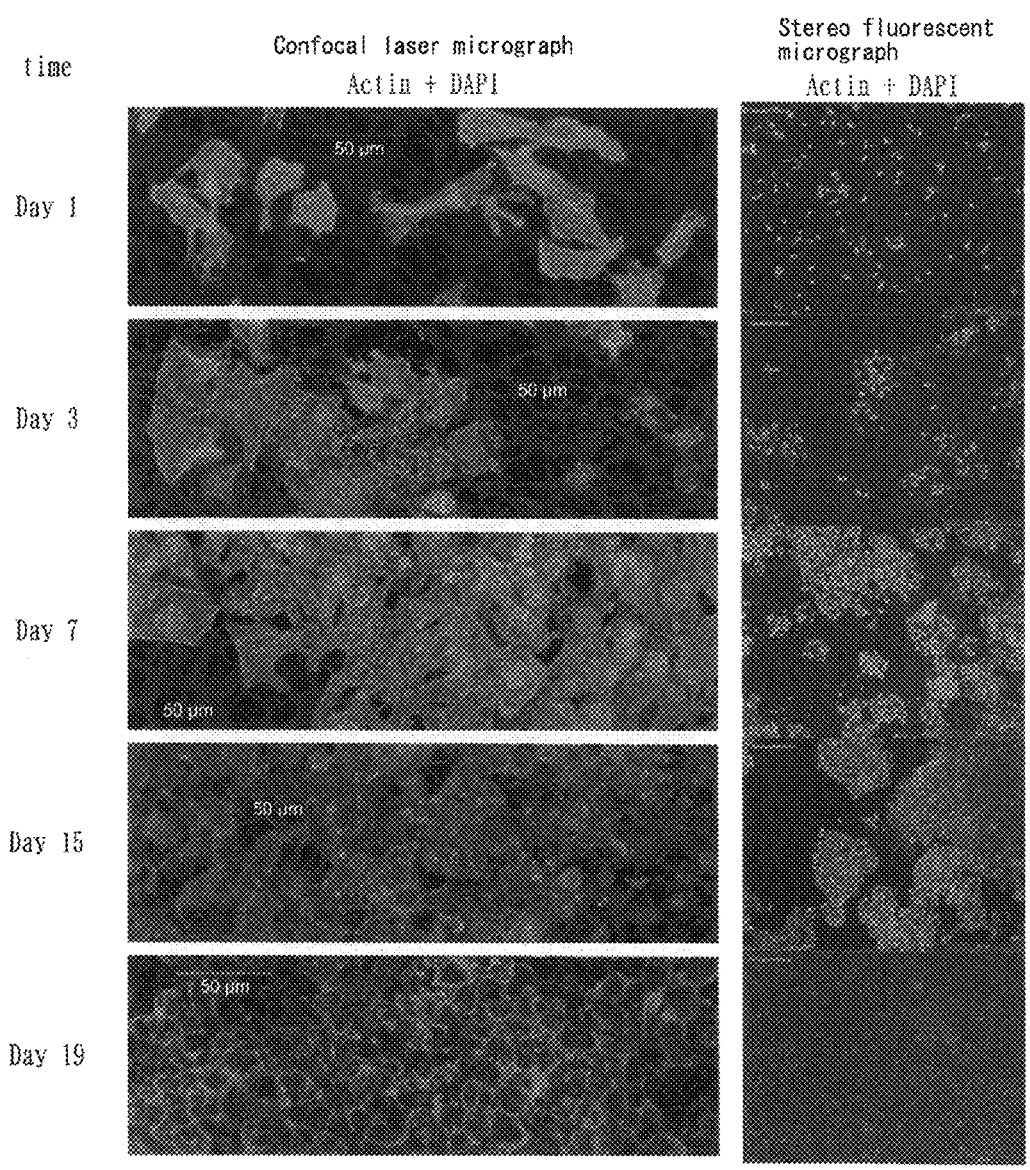
Figures 3, 15:
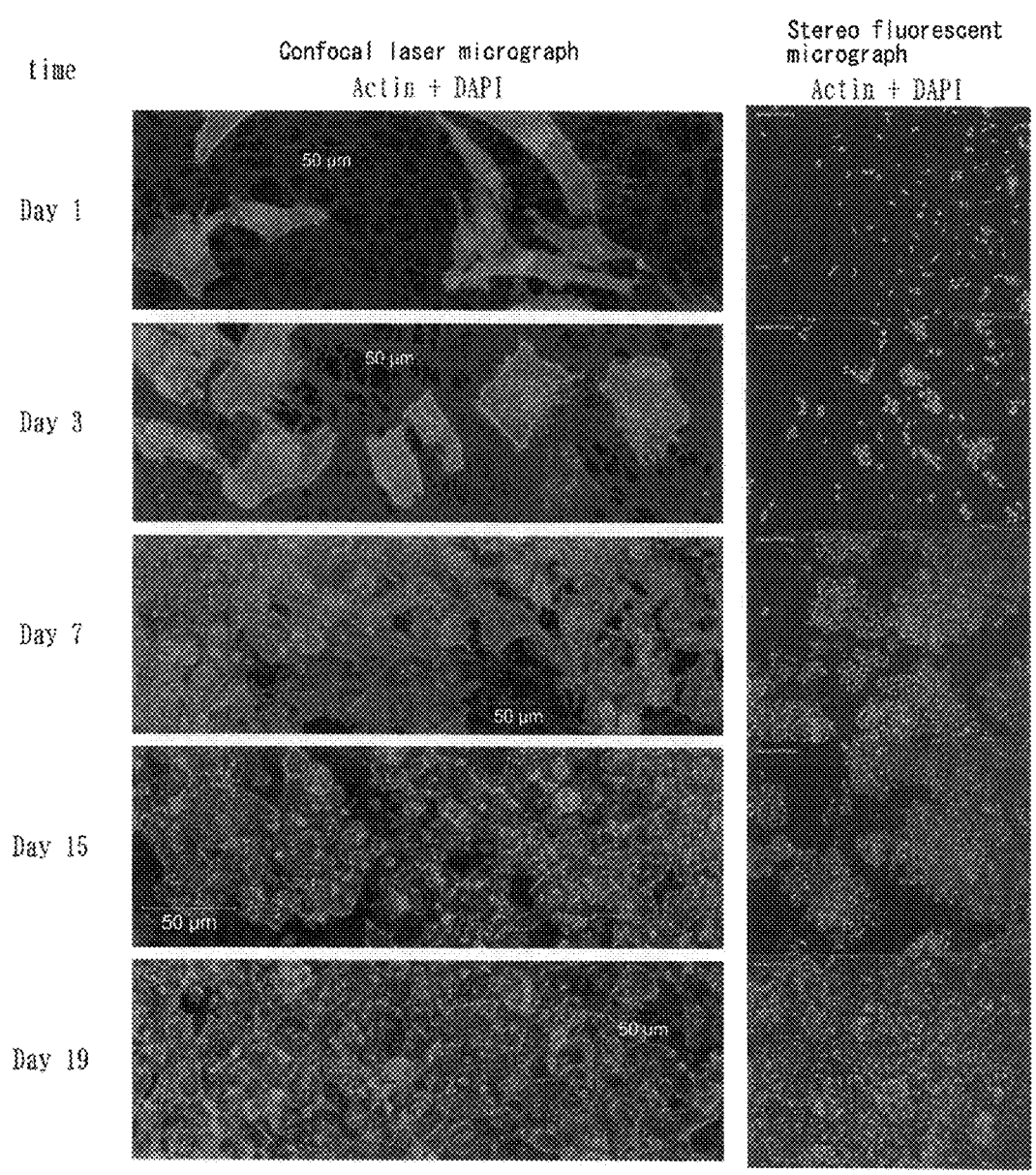

The results are shown in FIGS. 15-1 to 15-3. The results indicated that HeLa cells, a typical type of established cell line, can also be cultured by the method of the present invention.

Example 12: Culturing of CHO Cells

For this example, CHO cells were cultured by the method of the present invention using a porous polyimide film, and observed under a confocal microscope and a stereo fluorescent microscope. The porous polyimide films used were of the three types: 25 μm, 40 μm and 75 μm. The culturing period was 1 to 7 days, and the microscopes used and specific steps were as described in Example 10.

Figures 1, 16:
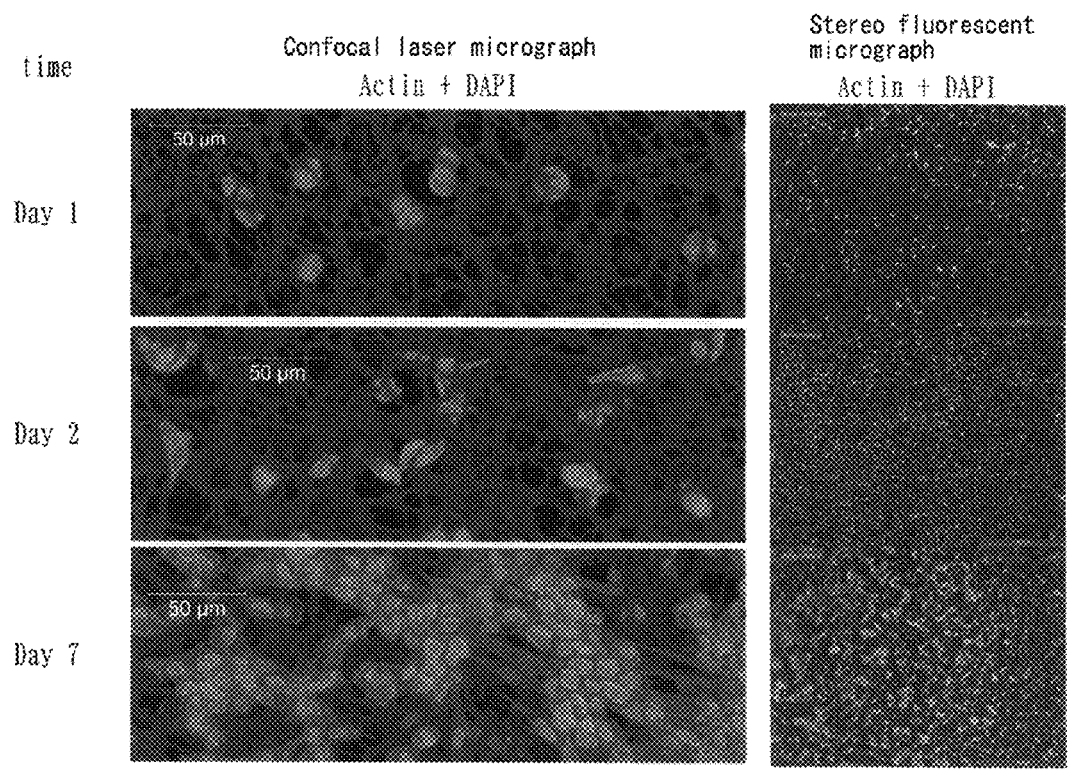
Figures 2, 16:
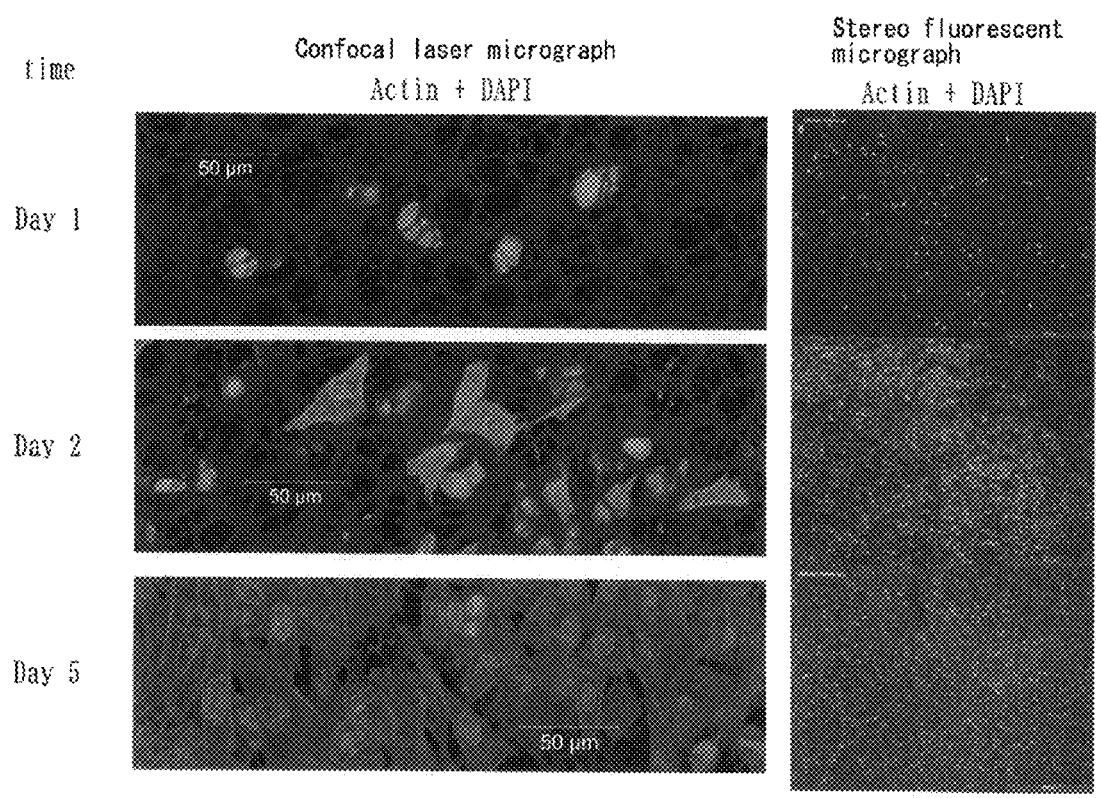
Figures 3, 16:
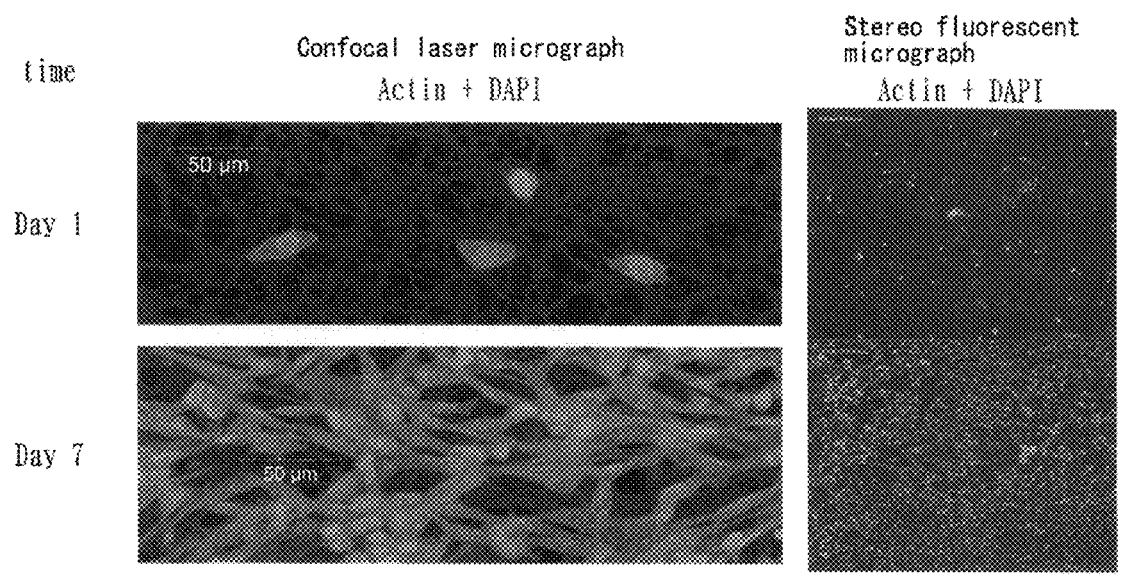

The results are shown in FIGS. 16-1 to 16-3. The results indicated that CHO cells, a typical type of established cell line, can also be cultured by the method of the present invention.

What is claimed is:

1. A cell culturing method that includes applying cells to a porous polyimide film and culturing them, wherein
    the porous polyimide film has a three-layer structure consisting of an A-surface layer having a plurality of pores, a B-surface layer having a plurality of pores, and a macro-void layer sandwiched between the two surface layers,
    a mean pore size in the A-surface layer is smaller than a mean pore size in the B-surface layer, and
    the macro-void layer has a partition bonded to the A-surface layer and the B-surface layer, and a plurality of macro-voids surrounded by the partition, the A-surface layer, and the B-surface layer.

2. The method according to claim 1, including a step of seeding cells on either the A-surface or the B-surface of the porous polyimide film.

3. The method according to claim 1, including a step of:
    placing a cell suspension on the dried surface of the porous polyimide film,
    allowing the porous polyimide film to stand, or moving the porous polyimide film to promote efflux of the liquid, or stimulating part of the surface to cause absorption of the cell suspension into the film, and
    retaining the cells in the cell suspension inside the film and allowing the water to flow out.

4. The method according to claim 1, including a step of:
    wetting one or both sides of the porous polyimide film with a cell culture medium or a sterilized liquid,
    loading a cell suspension into the wetted porous polyimide film, and
    retaining the cells in the cell suspension inside the film and allowing the water to flow out.

5. The method according to claim 4, wherein the viable cells are retained in the porous polyimide film, and the dead cells are allowed to flow out together with the water.

6. The method according to claim 4, wherein the sterilized liquid is sterilized water or a sterilized buffering solution.

7. The method according to claim 1, including the aspect that the cell culture medium, cells and one or more porous polyimide films are placed in a cell culturing vessel, wherein the porous polyimide film is in a suspended state in the cell culture medium.

8. The method according to claim 7, wherein two or more fragments of the porous polyimide film are used.

9. The method according to claim 7, wherein the cells spontaneously adhere to the porous polyimide film.

10. The method according to claim 1, wherein the porous polyimide film is:
    i) folded,
    ii) wound into a roll,
    iii) connected as sheets or fragments by a filamentous structure, or
    iv) bound into a rope,
for suspension or fixing in the cell culture medium in the cell culturing vessel.

11. The method according to claim 10, wherein the cells spontaneously adhere to the porous polyimide film.

12. The method according to claim 1, including using two or more porous polyimide films layered either above and below or left and right in the cell culture medium.

13. The method according to claim 1, wherein the cells grow and proliferate on the surface of and inside the porous polyimide film.

14. The method according to claim 1, wherein the cells are selected from the group consisting of animal cells, insect cells, plant cells, yeast cells and bacteria.

15. The method according to claim 14, wherein the animal cells are cells derived from an animal belonging to the subphylum Vertebrata.

16. The method according to claim 14, wherein the bacteria are selected from the group consisting of lactic acid bacteria, *E. coli, Bacillus subtilis* and cyanobacteria.

17. The method according to claim 1,
    wherein the cells are selected from the group consisting of pluripotent stem cells, tissue stem cells, somatic cells and germ cells.

18. The method according to claim 1, wherein the cells are selected from the group consisting of sarcoma cells, established cell lines and transformants.

19. The method according to claim 1, wherein the porous polyimide film is a porous polyimide film including a polyimide obtained from a tetracarboxylic dianhydride and a diamine.

* * * * *